(12) United States Patent
Chen

(10) Patent No.: US 6,765,008 B1
(45) Date of Patent: *Jul. 20, 2004

(54) PYRROLOPYRIMIDINES AS CRF ANTAGONISTS

(75) Inventor: Yuhpyng Liang Chen, Waterford, CT (US)

(73) Assignee: Pfizer Inc, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/448,539
(22) PCT Filed: Nov. 12, 1993
(86) PCT No.: PCT/US93/10715
  § 371 (c)(1),
  (2), (4) Date: Jun. 14, 1995
(87) PCT Pub. No.: WO94/13676
  PCT Pub. Date: Jun. 23, 1994

Related U.S. Application Data

(63) Continuation-in-part of application No. 07/991,764, filed on Dec. 17, 1992, now abandoned.

(51) Int. Cl.$^7$ .................... A61K 31/519; C07D 487/04
(52) U.S. Cl. .................... 514/265.1; 544/280
(58) Field of Search .................... 544/280; 514/258, 514/265.1

(56) References Cited

U.S. PATENT DOCUMENTS

| | | | |
|---|---|---|---|
| 4,229,453 A | * 10/1980 | Roth et al. | 424/251 |
| 4,605,642 A | 8/1986 | Rivier et al. | 514/12 |
| 5,002,950 A | * 3/1991 | Malone et al. | 514/258 |
| 5,063,245 A | 11/1991 | Abreu et al. | 514/404 |
| 5,153,352 A | 10/1992 | Norbeck et al. | 560/17 |

FOREIGN PATENT DOCUMENTS

| | | | |
|---|---|---|---|
| DE | 3145287 | * | 5/1983 |
| EP | 0475411 | | 3/1992 |
| EP | 0482804 | | 4/1992 |
| EP | 582804 A1 | | 4/1992 |

OTHER PUBLICATIONS

Marquet, J.P. et al. *Chem. Abstracts*, vol. 76, Abstract No. 126924 (1972) with RN 35800–96–5 and 35800–95–4.*
Marquet, J.-P. et al. *Chimie Therapeutique*, vol. 6, pp. 427–438 (1971).*
De Souza, E.B. *Psychoneuroendocrinology*, vol. 20, p. 789, 1995; abstract only from MEDLINE, Abstract No. 96431007.*
Wei, E.T. et al. *CIBA Foundation Symposium*, vol. 172, p. 258, 1993; abstract only from MEDLINE, Abstract No. 93259002.*
*Chem. Abstract.*, vol. 72, (1970), abstract No. 110080v.
Robbins et al., *Can. J. Chem.*, vol. 55, (1977), pp. 1251–1259.
Abdelhamid et al., *Rev. Port. Quim.*, vol. 27. (1985), pp. 500–504.
Folkers, G., *Deutsche Apotheker Zeitung*, vol. 126. (1986), pp. 2243–2247.
Jorgensen et al., *Chemica Scripta.*, vol. 24, (1984), pp. 73–79.
English Summary of Folkers, G., *Deutsche Apotheker Zeitung*, vol. 126. (1986), pp. 2243–2247.
English Abstract of DE 3145287 (1983).
Owens et al. *Pharm. Rev.*, vol. 43 (1991), pp 425–473.

* cited by examiner

Primary Examiner—Richard L. Raymond
(74) Attorney, Agent, or Firm—Paul H. Ginsburg

(57) ABSTRACT

The compounds of the formula

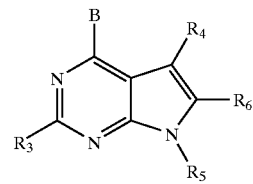

wherein $R_1$, $R_2$, $R_3$, $R_4$, $R_5$ and $R_6$ are as defined herein, are useful in the treatment of stress-related and other diseases. These compounds have corticotropin-releasing factor antagonist activity and as such are of use in the treatment of stress and anxiety related, and other disorders.

18 Claims, No Drawings

PYRROLOPYRIMIDINES AS CRF ANTAGONISTS

This application is a 371 of PCT/US93/10715, filed Nov. 12, 1993, which is a continuation-in-part of U.S. Ser. No. 07/991,764, which was filed on Dec. 17, 1992 now abandoned.

CROSS-REFERENCE TO RELATED APPLICATIONS

This application is a national phase of international application PCT/US93/10715, filed Nov. 12, 1993, which is a continuation-in-part of U.S. patent application Ser. No. 07/991,764, now abandoned, filed Dec. 17, 1992.

This invention relates to pyrrolopyrimidines, pharmaceutical compositions containing them, and their use in the treatment of stress-related and other diseases. The compounds have corticotropin-releasing factor (CRF) antagonist activity.

CRF antagonists are mentioned in U.S. Pat. Nos. 4,605,642 and 5,063,245 referring to peptides and pyrazolinones, respectively. The importance of CRF antagonists is set out in the literature, e.g. as discussed in U.S. Pat. No. 5,063,245, which is incorporated herein by reference. A recent outline of the different activities possessed by CRF antagonists is found in M. J. Owens et al., Pharm. Rev., Vol. 43, pages 425 to 473 (1991), also incorporated herein by reference. Based on the research described in these two and other references, CRF antagonists are considered effective in the treatment of a wide range of diseases including stress-related illnesses, such as stress-induced depression, anxiety, and headache; irritable bowel syndrome; inflammatory diseases; immune suppression; human immunodeficiency virus (HIV) infections; Alzheimer's disease; gastrointestinal diseases; anorexia nervosa; hemorrhagic stress; drug and alcohol withdrawal symptoms; drug addiction, and fertility problems.

The present invention relates to a compound of the formula

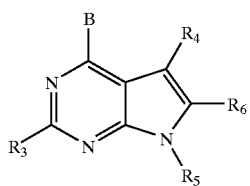

(I)

and the acid addition salts thereof, wherein

B is XA wherein X is $(CH_2)_n$ in which n is 0, 1 or 2, NH, O, S, or N($C_1$–$C_4$ alkyl);

A is $NR_1R_2$, $CR_1R_2R_{11}$, or $C(=CR_2R_{12})R_1$;

$R_1$ is hydrogen, or mono or divalent $C_1$–$C_6$ aliphatic hydrocarbon which may be substituted by one or two substituents $R_7$ independently selected from the group consisting of hydroxy, fluoro, chloro, bromo, iodo, $C_1$–$C_8$ alkoxy, O—C(=O)—($C_1$–$C_6$ alkyl), O—C(=O)—NH($C_1$–$C_4$ alkyl), O—C(=O)—N($C_1$–$C_4$ alkyl)($C_1$–$C_2$ alkyl), amino, NH($C_1$–$C_4$ alkyl), N($C_1$–$C_2$ alkyl)($C_1$–$C_4$ alkyl), S($C_1$–$C_6$ alkyl), N($C_1$–$C_4$ alkyl)($C_1$–$C_4$ alkyl), NH($C_1$–$C_4$ alkyl), COOH, O($C_1$–$C_4$ alkyl), NH($C_1$–$C_4$ alkyl), N($C_1$–$C_4$ alkyl)($C_1$–$C_2$ alkyl), SH, CN, $NO_2$, SO($C_1$–$C_4$ alkyl), $SO_2$($C_1$–$C_4$ alkyl $SO_2$NH($C_1$–$C_4$ alkyl), $SO_2$N($C_1$–$C_4$ alkyl)($C_1$–$C_2$ alkyl), and said mono or divalent $C_1$–$C_6$ aliphatic hydrocarbon may contain one or two double or triple bonds;

$R_2$ is monovalent $C_1$–$C_{12}$ aliphatic hydrocarbon, aryl or (divalent $C_1$–$C_{10}$ aliphatic hydrocarbon)aryl wherein said aryl is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzisothiazolyl, thiazolyl, isoxazolyl, benzisoxazolyl, benzimidazolyl, triazolyl, pyrazolyl, pyrrolyl, indolyl, pyrrolopyridyl, oxazolyl, or benzoxazolyl; 3- to 8-membered cycloalkyl or ($C_1$–$C_6$ alkylene) cycloalkyl, wherein one or two methylene groups of said cycloalkyl may be independently replaced by one or two O, S or N—Z radicals wherein Z is hydrogen, $C_1$–$C_4$ alkyl, benzyl or $C_1$–$C_4$ alkanoyl, wherein $R_2$ may be substituted independently by from one to three of chloro, fluoro, or $C_1$–$C_4$ alkyl, or one of hydroxy, bromo, iodo, $C_1$–$C_6$ alkoxy, O—C(=O)—($C_1$–$C_6$ alkyl), O—C—N($C_1$–$C_4$ alkyl)($C_1$–$C_2$ alkyl), S($C_1$–$C_6$ alkyl), $NH_2$, NH($C_1$–$C_2$ alkyl), N($C_1$–$C_2$ alkyl) ($C_1$–$C_4$ alkyl), N($C_1$–$C_4$ alkyl)—C(=O)—($C_1$–$C_4$ alkyl), NHC(=O)($C_1$–$C_4$ alkyl), COOH, C(=O)—O($C_1$–$C_4$ alkyl), C(=O)NH($C_1$–$C_4$ alkyl), C(=O)N($C_1$–$C_4$ alkyl)($C_1$–$C_2$ alkyl), SH, CN, $NO_2$, SO($C_1$–$C_4$ alkyl), $SO_2$($C_1$–$C_4$ alkyl), $SO_2$NH($C_1$–$C_4$ alkyl), $SO_2$N($C_1$–$C_4$ alkyl)($C_1$–$C_2$ alkyl), and wherein said monovalent $C_1$–$C_{12}$ aliphatic hydrocarbon or said divalent $C_1$–$C_{10}$ aliphatic hydrocarbon may contain one to three double or triple bonds; or when A is $NR_1R_2$ or $CR_1R_2R_{11}$, the $R_1$ and $R_2$ may be taken together with the atom to which they are attached to form a saturated 4- to 8-membered ring optionally containing one or two double bonds or one or two O, S or N—Z radicals wherein Z is hydrogen, $C_1$–$C_4$ alkyl, or $C_1$–$C_4$ alkanoyl;

$R_3$ is hydrogen, monovalent $C_1$–$C_6$ aliphatic hydrocarbon, fluoro, chloro, bromo, iodo, hydroxy, amino, O(monovalent $C_1$–$C_6$ aliphatic hydrocarbon), NH(monovalent $C_1$–$C_4$ aliphatic hydrocarbon), N(monovalent $C_1$–$C_4$ aliphatic hydrocarbon)($C_1$–$C_2$ alkyl), SH, S(monovalent $C_1$–$C_4$ aliphatic hydrocarbon), SO(monovalent $C_1$–$C_4$ aliphatic hydrocarbon), or $SO_2$(monovalent $C_1$–$C_4$ aliphatic hydrocarbon), wherein said monovalent $C_1$–$C_4$ aliphatic hydrocarbon and said monovalent $C_1$–$C_6$ aliphatic hydrocarbon may contain one or two double or triple bonds and may be substituted by one to three substituents $R_8$ independently selected from the group consisting of hydroxy, amino, $C_1$–$C_3$ alkoxy, dimethylamino, diethylamino, methylamino, ethylamino, NHC(=O)$CH_3$, fluoro, chloro and $C_1$–$C_3$ alkylthio;

$R_4$ and $R_6$ are each independently hydrogen, $C_1$–$C_6$ alkyl, fluoro, chloro, bromo, iodo, $C_1$–$C_6$ alkoxy, amino, NH($C_1$–$C_6$ alkyl), N($C_1$–$C_6$ alkyl)($C_1$–$C_2$ alkyl), $SO_n$ ($C_1$–$C_6$ alkyl) wherein n is 0, 1 or 2, cyano, hydroxy, carboxy, or amido, wherein said $C_1$–$C_6$ alkyls may be substituted by one to three of hydroxy, amino, carboxy, amido, NHC(=O)($C_1$–$C_4$ alkyl), NH($C_1$–$C_4$ alkyl), N($C_1$–$C_4$ alkyl)($C_1$–$C_2$ alkyl), C(=O)O($C_1$–$C_4$ alkyl), $C_1$–$C_3$ alkoxy, $C_1$–$C_3$ alkylthio, fluoro, bromo, chloro, iodo, cyano or nitro;

$R_5$ is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzoisothiazolyl, thiazolyl, isoxazolyl, benzisoxazolyl, benzimidazolyl, triazolyl, pyrazolyl, pyrrolyl, indolyl, azaindolyl, benzoxazolyl, oxazolyl, pyrrolidinyl, thiazolidinyl, morpholinyl, piperidinyl, piperazinyl, tetrazolyl, or 3- to 8-membered cycloalkyl or 9- to 12-membered bicycloalkyl, optionally containing one to three O, S or N—Z radicals wherein Z is hydrogen, $C_1$–$C_4$ alkyl, $C_1$–$C_4$ alkanoyl, phenyl or phenylmethyl, wherein each one of the above groups may be substituted independently by from one to four of fluoro, chloro, monovalent $C_1$–$C_6$ aliphatic hydrocarbon, $C_1$–$C_6$ alkoxy or trifluoromethyl, or one of bromo, iodo, cyano, nitro, amino, NH(monovalent $C_1$–$C_4$ aliphatic hydrocarbon), N(monovalent $C_1$–$C_4$ aliphatic hydrocarbon)($C_1$–$C_2$ alkyl), COO (monovalent $C_1$–$C_4$ aliphatic hydrocarbon), CO(monovalent $C_1$–$C_4$ aliphatic hydrocarbon), $SO_2$NH(monovalent $C_1$–$C_4$ aliphatic hydrocarbon), $SO_2$N(monovalent $C_1$–$C_4$ aliphatic hydrocarbon) ($C_1$–$C_2$ alkyl), $SO_2NH_2$, $NHSO_2$(monovalent $C_1$–$C_4$ aliphatic hydrocarbon), S(monovalent $C_1$–$C_6$ aliphatic hydrocarbon), $SO_2$(monovalent $C_1$–$C_6$ aliphatic hydrocarbon), wherein said monovalent $C_1$–$C_4$ aliphatic hydrocarbon and said monovalent $C_1$–$C_6$ aliphatic hydrocarbon may be substituted by one or two of fluoro, chloro, hydroxy, amino, methylamino, dimethylamino or acetyl;

$R_{11}$ is hydrogen, hydroxy, fluoro, chloro, COO($C_1$–$C_2$ alkyl), cyano, or CO($C_1$–$C_2$ alkyl); and $R_{12}$ is hydrogen or monovalent $C_1$–$C_4$ aliphatic hydrocarbon; with the proviso that (1) when $R_5$ is pbromophenyl, and at least two of $R_3$, $R_4$ and $R_6$ are methyl, then B is not ethyl, ethoxy, S-ethyl, methylamino, dimethylamino, or hydroxyethylamino; and (2) when $R_5$ is unsubstituted phenyl or unsubstitued cycloalkyl, then at least one of $R_3$ and $R_4$ is methyl, and B is not benzylamino, furfuryl (furanylmethyl)amino, or anilino (phenylamino).

Preferred compounds of the formula I of the invention are those wherein $R^1$ is monovalent $C_1$–$C_6$ aliphatic hydrocarbon, which may be substituted by one or two of substituents $R_7$ independently selected from the group consisting of hydroxy, fluoro, chloro, $C_1$–$C_2$ alkoxy, and OC—O—($C_1$–$C_2$ alkyl); those wherein $R_2$ is monovalent $C_2$–$C_6$ aliphatic hydrocarbon or ethylenephenyl; those wherein $R_3$ is hydrogen, methyl, ethyl, fluoro, chloro or methoxy; those wherein $R_4$ and $R_6$ are independently hydrogen, methyl, or ethyl; and those wherein $R_5$ is phenyl substituted by two or three substituents, specifically 2,4,6-trichlorophenyl, 2,6-dichloro-4-trifluoromethyl, 2,4,6-trimethylphenyl, 2,4-dimethylphenyl, 2,6-dimethylphenyl, 2-methyl-4-iodophenyl, or 3,5-ditrifluoromethylphenyl.

Specific preferred compounds include:
n-butyl-ethyl-[2,5-dimethyl-7-(2,4,6-trimethylphenyl)-7H-pyrrolo[2,3-d]pyrimidin-4-yl]amine;
di-n-propyl-[2,5-dimethyl-7-(2,4,6-trimethylphenyl)-7H-pyrrolo[2,3-d]pyrimidin-4-yl]amine;
ethyl-n-propyl-[2,5-dimethyl-7-(2,4,6-trimethylphenyl)-7H-pyrrolo[2,3-d]pyrimidin-4-yl]amine;
diethyl-2,5-dimethyl-7-(2,4,6-trimethylphenyl)-7H-pyrrolo[2,3-d]pyrimidin-4-yl]amine;
n-butyl-ethyl-[2,5,6-trimethyl-7-(2,4,6-trimethylphenyl)-7H-pyrrolo[2,3-d]pyrimidin-4-yl]amine;
2-(N-n-butyl-N-[2,5-dimethyl-7-(2,4,6-trimethyl phenyl)-7H-pyrrolo[2,3-d]pyrimidin-4-yl]amino}-ethanol;
4-(1-ethyl-propyl)-2,5,6-trimethyl-7-(2,4,6-trimethylphenyl)-7H-pyrrolo[2,3-d]pyrimidine;
n-butyl-ethyl-[2,5-dimethyl-7-(2,4-dimethylphenyl)-7H-pyrrolo[2,3-d]pyrimidin-4-yl]amine; and
2,5-dimethyl-7-(2,4,6-trimethylphenyl)-7H-pyrrolo[2,3-d]pyrimidyl-4-yl-(1-ethyl-propyl)amine.

The invention also relates to a pharmaceutical composition for the treatment of illnesses induced or facilitated by corticotropin releasing factor which comprises a compound of the formula I as defined above in an amount effective in the treatment of said illnesses, and a pharmaceutically acceptable carrier, and a pharmaceutical composition for the treatment of inflammatory disorders, stress and anxiety related disorders including stress-induced depression and headache, irritable bowel syndrome, immune suppression, human immunedeficiency virus (HIV) infections, Alzheimer's disease, gastrointestinal diseases, anorexia nervosa, hemorrhagic stress, drug and alcohol withdrawal symptoms, drug addiction, and fertility problems, which comprises a compound of the formula I as defined above in an amount effective in the treatment of said disorders, and a pharmaceutically acceptable carrier. Preferred compositions of the invention are those containing preferred compounds of formula I as described above.

The invention further relates to a method for the treatment of illnesses induced or facilitated by corticotropin releasing factor by administering to a subject in need of such treatment a compound of formula I as defined above in an amount effective in such treatment, and a method for the treatment of stress and anxiety related disorders including stress-induced depression and headache, irritable syndrome, inflammatory disorders, immune suppression, human immunedeficiency virus (HIV) infections, Alzheimer's disease, gastrointestinal diseases, anorexia nervosa, hemorrhagic stress, drug and alcohol withdrawal symptoms, drug addiction, and fertility problems, particularly depression, by administering to a subject in need of such treatment a compound of formula I as defined above in an amount effective in such treatment. Preferred methods of the invention are those administering a preferred compound of the formula I as described above.

The invention also relates to an intermediate compound of the formula

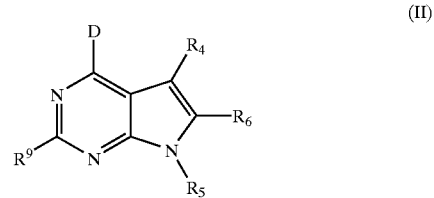

(II)

wherein
D is hydroxy or chloro,
$R_4$ and $R_6$ are each independently hydrogen, $C_1$–$C_6$ alkyl, fluoro, chloro, bromo, iodo, $C_1$–$C_6$ alkoxy, amino, NH($C_1$–$C_6$ alkyl), N($C_1$–$C_6$ alkyl)($C_1$–$C_2$ alkyl), $SO_n$ ($C_1$–$C_6$ alkyl), wherein n is 0, 1 or 2, cyano, hydroxy, carboxy, or amido, wherein said $C_1$–$C_6$ alkyls may be substituted by one to three of hydroxy, amino, carboxy, amido, NHC(=O)($C_1$–$C_4$ alkyl), NH($C_1$–$C_4$ alkyl), N($C_1$–$C_4$ alkyl)($C_1$–$C_2$ alkyl), C(=O)O($C_1$–$C_4$ alkyl), $C_1$–$C_3$ alkoxy, $C_1$–$C_3$ alkylthio, fluoro, bromo, chloro, iodo, cyano or nitro;
$R_5$ is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzoisothiazolyl, thiazolyl, isoxazolyl, benzisoxazolyl, benzimidazolyl, triazolyl, pyrazolyl, pyrrolyl, indolyl, azaindolyl, benzoxazolyl, oxazolyl, pyrrolidinyl, thiazolidinyl, morpholinyl, piperdinyl, piperazinyl, tetrazolyl, or 3- to 8-membered cycloalkyl or 9- to 12-membered bicycloalkyl, optionally containing one to three of O, S or N—Z wherein Z is hydrogen, $C_1$–$C_4$ alkyl, $C_1$–$C_4$ alkanoyl, phenyl or phenylmethyl, wherein each of the above groups may be substituted independently by from one to four of fluoro, chloro, $C_1$–$C_6$ alkyl, $C_1$–$C_6$ alkoxy or trifluoromethyl, or one of bromo, iodo, cyano, nitro, amino, NH($C_1$–$C_4$ alkyl), N($C_1$–$C_4$)($C_1$–$C_2$ alkyl), COO($C_1$–$C_4$ alkyl), CO($C_1$–$C_4$ alkyl), $SO_2$NH($C_1$–$C_4$ alkyl), $SO_2$N($C_1$–$C_4$ alkyl)($C_1$–$C_2$ alkyl), $SO_2NH_2$, $NHSO_2$($C_1$–$C_4$), S($C_1$–$C_6$ alkyl), $SO_2$($C_1$–$C_6$ alkyl), wherein said $C_1$–$C_4$ alkyl and $C_1$–$C_6$ alkyl may be substituted by one or two of fluoro, chloro, hydroxy, amino, methylamino, dimethylamino or acetyl; with the proviso that $R_5$ is not unsubstituted phenyl; and $R_9$ is hydrogen, $C_1$–$C_6$ alkyl or chloro, and a compound of the formula

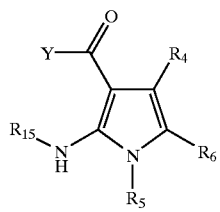

(V)

wherein

Y is $CR_1R_2R_{11}$, $CH_2A$ or $(CH_2)_2A$;

A is $NR_1R_2$, $CR_1R_2R_{11}$ or $C(=CR_2R_{12})R_1$;

$R_1$ is hydrogen, or monovalent $C_1$–$C_6$ aliphatic hydrocarbon which may be substituted by one or two substituents $R_7$ independently selected from the group consisting of hydroxy, fluoro, chloro, bromo, iodo, $C_1$–$C_8$ alkoxy, O—C(=O)—($C_1$–$C_6$ alkyl), O—C(=O)NH($C_1$–$C_4$ alkyl), O—C(=O)—N($C_1$–$C_4$ alkyl)($C_1$–$C_2$ alkyl), amino, NH($C_1$–$C_4$ alkyl), N($C_1$–$C_2$ alkyl) ($C_1$–$C_4$ alkyl), S($C_1$–$C_6$ alkyl), N($C_1$–$C_4$alkyl)C(=O)($C_1$–$C_4$ alkyl), NHC(=O)($C_1$–$C_4$ alkyl), COOH, C(=O)O($C_1$–$C_4$ alkyl), C(=O)NH($C_1$–$C_4$ alkyl), C(=O)N($C_1$–$C_4$ alkyl)($C_1$–$C_2$ alkyl), SH, CN, $NO_2$, SO($C_1$–$C_4$ alkyl), $SO_2$($C_1$–$C_4$ alkyl), $SO_2$NH($C_1$–$C_4$ alkyl), $SO_2$N($C_1$–$C_4$ alkyl)($C_1$–$C_2$ alkyl), and said monovalen $C_1$–$C_6$ aliphatic hydrocarbon may contain one or two double or triple bonds;

$R_2$ is monovalent $C_1$–$C_{12}$ aliphatic hydrocarbon, aryl or (divalent $C_1$–$C_{10}$ aliphatic hydrocarbon)aryl wherein said aryl is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzisothiazolyl, thiazolyl, isoxazolyl, benzisoxazolyl, benzimidazolyl, triazolyl, pyrazolyl, pyrrolyl, indolyl, azaindolyl, oxazolyl, or benzoxazolyl; 3- to 8-membered cycloalkyl or ($C_1$–$C_6$ alkylene) cycloalkyl, wherein said cycloalkyl may contain one or two of O, S or N—Z wherein Z is hydrogen, $C_1$–$C_4$ alkyl, benzyl or $C_1$–$C_4$ alkanoyl, wherein $R_2$ may be substituted independently by from one to three of chloro, fluoro, or $C_1$–$C_4$ alkyl, or one of hydroxy, bromo, iodo, $C_1$–$C_6$ alkoxy, O—C(=O)—($C_1$–$C_6$ alkyl), O—C—N($C_1$–$C_4$ alkyl)($C_1$–$C_2$ alkyl), S($C_1$–$C_6$ alkyl), $NH_2$, NH($C_1$–$C_2$ alkyl), N($C_1$–$C_2$ alkyl) ($C_1$–$C_4$ alkyl), N($C_1$–$C_4$)—C(=O)($C_1$–$C_4$ alkyl), NHC(=O) ($C_1$–$C_4$), COOH, C(=O)O($C_1$–$C_4$ alkyl), C(=O)NH ($C_1$–$C_4$ alkyl), C(=O)N($C_1$–$C_4$ alkyl)($C_1$–$C_2$ alkyl), SH, CN, $NO_2$, SO($C_1$–$C_4$ alkyl), $SO_2$($C_1$–$C_4$ alkyl), $SO_2$NH($C_1$–$C_4$ alkyl), $SO_2$N($C_1$–$C_4$ alkyl)$C_1$–$C_2$ alkyl), and wherein said monovalent $C_1$–$C_{12}$ aliphatic hydrocarbon or said divalent $C_1$–$C_{10}$ aliphatic hydrocarbon may contain one to three double or triple bonds; or when A is $NR_1R_2$ or $CR_1R_2R_{11}$, then $R_1$ and $R_2$ taken together with the atom to which they are attached may form a saturated 4- to 8-membered optionally containing one or two double bonds or one or two of O, S or N—Z wherein Z is hydrogen, $C_1$–$C_4$ alkyl, or $C_1$–$C_4$ alkanoyl;

$R_3$ is hydrogen, $C_1$–$C_6$ alkyl, fluoro, chloro, bromo, iodo, hydroxy, amino, O($C_1$–$C_6$ alkyl), NH($C_1$–$C_6$ alkyl), N($C_1$–$C_4$ alkyl)($C_1$–$C_2$ alkyl), SH, S($C_1$–$C_4$ alkyl), SO($C_1$–$C_4$ alkyl), or $SO_2$($C_1$–$C_4$ alkyl), wherein said $C_1$–$C_4$ alkyl and $C_1$–$C_6$ alkyl may contain from one or two double or triple bonds and may be substituted by from 1 to 3 substituents $R_8$ independently selected from the group consisting of hydroxy, amino, $C_1$–$C_3$ alkoxy, dimethylamino, diethylamino, methylamino, ethylamino, NHC(=O)$CH_3$, fluoro, chloro or $C_1$–$C_3$ alkylthio;

$R_4$ and $R_6$ are each independently hydrogen, $C_1$–$C_6$ alkyl, fluoro, chloro, bromo, iodo, $C_1$–$C_6$ alkoxy, amino, NH($C_1$–$C_6$ alkyl), N($C_1$–$C_6$ alkyl)($C_1$–$C_2$ alkyl), $SO_n$ ($C_1$–$C_6$ alkyl), wherein n is 0, 1 or 2, cyano, hydroxy, carboxy, or amido, wherein said $C_1$–$C_6$ alkyls may be substituted by one to three of hydroxy, amino, carboxy, amido, NHC(=O)($C_1$–$C_4$ alkyl), NH($C_1$–$C_4$ alkyl), N($C_1$–$C_4$ alkyl)($C_1$–$C_2$ alkyl), C(=O)O($C_1$–$C_4$ alkyl), $C_1$–$C_3$ alkoxy, $C_1$–$C_3$ alkylthio, fluoro, bromo, chloro, iodo, cyano or nitro;

$R_5$ is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzisothiazolyl, thiazolyl, isoxazolyl, benzisoxazolyl, benzimidazolyl, triazolyl, pyrazolyl, pyrrolyl, indolyl, azaindolyl, benzoxazolyl, oxazolyl, pyrrolidinyl, thiazolidinyl, morpholinyl, piperidinyl, piperazinyl, tetrazolyl, or 3- to 8-membered cycloalkyl or 9- to 12-membered bicycloalkyl, optionally containing one to three of O, S or N—Z wherein Z is hydrogen, $C_1$–$C_4$ alkyl, $C_1$–$C_4$ alkanoyl, phenyl or phenylmethyl, wherein each one of the above groups may be substituted independently by from one to four of fluoro, chloro, $C_1$–$C_6$ alkyl, $C_1$–$C_6$ alkoxy or trifluoromethyl, or one of bromo, iodo, cyano, nitro, amino, NH($C_1$–$C_4$ alkyl), N($C_1$–$C_4$)($C_1$–$C_2$ alkyl), COO($C_1$–$C_4$ alkyl), CO($C_1$–$C_4$ alkyl), $SO_2$NH($C_1$–$C_4$ alkyl), $SO_2$N($C_1$–$C_4$ alkyl)($C_1$–$C_2$ alkyl), $SO_2NH_2$, $NHSO_2$($C_1$–$C_4$ alkyl), S($C_1$–$C_6$ alkyl), $SO_2$($C_1$–$C_6$ alkyl), wherein said $C_1$–$C_4$ alkyl and $C_1$–$C_6$ alkyl may be substituted by one or two of fluoro, chloro, hydroxy, amino, methylamino, dimethylamino or acetyl; with the proviso that $R_5$ is not unsubstituted phenyl;

$R_{11}$ is hydrogen, hydroxy, fluoro, chloro, COO($C_1$–$C_2$ alkyl), cyano, or CO($C_1$–$C_2$ alkyl); and $R_{12}$ is hydrogen or $C_1$–$C_4$ alkyl.

Whenever reference is made herein to 3- to 8-membered cycloalkyl or 9- to 12-membered bicycloalkyl containing one to three of O, S or N—Z, it is understood that the oxygen and sulfur ring atoms are not adjacent to each other. The three membered cycloalkyl has just one O, S or N—Z. An example of a six-membered cycloalkyl having O and N is morpholinyl.

Whenever $R_2$ or $R_5$ is a heterocyclic group, the attachment of the group is through a carbon atom.

The terms "monovalent aliphatic hydrocarbon" and "divalent aliphatic hydrocarbon" have been used herein, usually associated with an indication of the number of carbon atoms present, e.g., "monovalent $C_1$–$C_{12}$ aliphatic hydrocarbon". These terms have been used herein to define $R_1$, $R_2$, $R_3$, and $R_5$, where they have also been associated with an indication that they include, optionally, unsaturation as well as with an expression of what type and extent of unsaturation is contemplated, e.g., by such language as "may contain one or two double or triple bonds". The term "aliphatic hydrocarbon" as thus used is intended to mean a straight or branched chain of carbon and hydrogen atoms that has a linear conformation rather than a cyclic or ring conformation, which is characteristic of aromatic hydrocarbons.

The aliphatic hydrocarbon chain may be saturated, i.e., it is an alkane, or it may be unsaturated, i.e., it is an alkene (double bond) or an alkyne (triple bond). It will be understood that where the aliphatic hydrocarbon is unsaturated by reason of the presence of one double or triple bond, that at least two carbon atoms are required to be present in the hydrocarbon chain; and that where two or more double and/or triple bonds are present, that at least three or more carbon atoms will be required in the hydrocarbon chain. The aliphatic hydrocarbon chain may also be monovalent or divalent. Where it is monovalent, it is a radical, e.g., where $R_2$ is defined as "monovalent $C_1$–$C_{12}$ aliphatic hydrocarbon", the $R_2$ substituent comprises an alkane-yl (alkyl), alkene-yl or alkyne-yl moiety directly attached to the nucleus of the compound of formula I by a single, covalent bond. Where the aliphatic hydrocarbon is divalent, it is a bridging element, e.g., where $R_2$ is defined as "(divalent $C_1$–$C_{10}$ aliphatic hydrocarbon)aryl", the $R_2$ substituent comprises an alkane-di-yl, alkene-di-yl or alkyne-di-yl moiety attached to said nucleus by a single, covalent bond, and at the same time attached to the "aryl" moiety by a single, covalent bond, whereby it forms a bridge between said aryl moiety and said nucleus.

Whenever reference is made herein to "amido" as a substituent moiety, e.g., in the definitions of substituents $R_4$ and $R_6$ to the nucleus of the compounds of formula I, it is understood that there is included within the meaning of that term as used herein a substituent moiety having one of the following formulas: —C(=O)NH$_2$; —C(=O)NH(C$_1$–C$_4$ alkyl); or —C(=O)N(C$_1$–C$_4$ alkyl)(C$_1$–C$_2$ alkyl).

The compounds of formula I wherein B is $NR_1R_2$, NHA, $N(C_1$–$C_4$ alkyl)A, OA, SA, A is $NR_1R_2$, $CR_1R_2R_{11}$ or $C(=CR_2R_{12})R_1$, and $R_3$ is hydrogen, $C_1$–$C_6$ alkyl or chloro (hereafter $R_9$) may be prepared by reaction of a compound of the formula

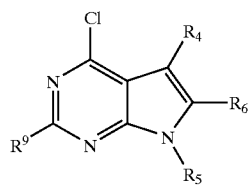

(II')

wherein $R_4$ and $R_5$ are as defined above with reference to formula I, with an amine of the formula $NHR_1R_2$, $NH_2A$, $NH(C_1$–$C_4$ alkyl)A, HOA or HSA wherein $R_1$ and $R_2$ are as defined with reference to formula I. The reaction is carried out in a solvent in the presence of a base at a temperature of between about 0° to about 150° C. Suitable solvents are organic solvents such as acetonitrile, dimethylsulfoxide, acetone, $C_2$–$C_{15}$ alkyl alcohol, tetrahydrofuran, chloroform, benzene, xylene or toluene, preferably acetontrile or dimethylsulfoxide.

When B is NHA, $NR_1R_2$ or $N(C_1$–$C_4$ alkyl)A, an excess of $NH_2A$, $NHR_1R_2$ or $NH(C_1$–$C_4$ alkyl)A, respectively, is used. Other bases such as potassium carbonate or tri-$(C_1$–$C_6)$alkyl amine may be used. The reaction is carried out at a temperature of about 75° to 150° C. When the reaction is carried out in the presence of a base, such as sodium hydride or potassium $C_1$–$C_4$ alkoxide, a molar equivalent of the amine is used. When B is OA or SA, a base which is capable of deprotonation of HOA or HSA may be used, such as an alkali metal hydride such as sodium hydride, or an organometallic base such as sodium diisopropylamide, sodium bis(trimethylsily)amide, lithium diisopropylamide, lithium bis(trimethylsily)amide, sodium $C_1$–$C_4$ alkoxide or n-butylithium. The solvent used is dry tetrahydrofuran, dimethylsulfoxide or methylene chloride, and the reaction temperature is between about −78° C. and the reflux temperature of the reaction mixture, preferably 0° C. to 80° C.

The compounds of formula I wherein B is $NR_1R_2$, NHA, $N(C_1$–$C_4$ alkyl)A, OA, SA and A is $NR_1R_2$, $CR_1R_2R_{11}$ or $C(=CR_2R_{12})R_1$ and $R_3$ is the groups other than $R_9$ (hereafter $R_{10}$) may be prepared by reacting a compound of the formula I wherein $R_3$ is chloro with a nucleophile of the formula $R_{10}H$ with or without an organic or inorganic base. Suitable bases include sodium, sodium hydride, and alkali metal hydroxide such as potassium hydroxide, and weaker bases such as potassium carbonate or triethylamine. The latter are generally used when $R_{10}H$ is alkanol, $C_1$–$C_6$ alkanethiol, an amine, e.g. $NH(C_1$–$C_6$ alkyl), or tetrahydrobutyl ammonium fluoride. Suitable solvents are dimethylsulfoxide, acetonitrile, $C_1$–$C_5$ alkyl alcohol, tetrahydrofuran, benzene, toluene or methylene chloride.

The compounds of formula II as defined above may be prepared by reacting the corresponding 4-hydroxy compound of formula III (not shown) with an excess of phosphorus oxychloride or thionyl chloride at temperatures between about 60 to 140° C., conveniently at the reflux temperature of the reaction mixture. When the reaction is carried out in a solvent, suitable solvents are halogenated alkanes, such as methylene chloride or chloroform. The reaction may be in the presence of a base such as N,N-diethylaniline, trimethylamine or potassium carbonate.

The compounds of formula III as defined above may be prepared by conventional methods as described in the prior art. Alternatively, the compounds of formula III wherein $R_9$ is hydrogen may be prepared by reaction of a compound of the formula

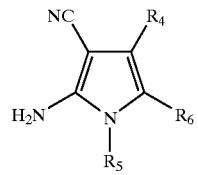

(IV)

wherein $R_4$, $R_5$, and $R_6$ are as defined with reference to formula I with formic acid at a temperature between about 60 to 140° C., preferably at the reflux temperature of the reaction mixture.

The compounds of formula III wherein $R_9$ is $C_1$–$C_6$ alkyl (hereafter $R_{13}$) may be prepared by reacting a compound of formula IV with $R_{13}COOCOR_{13}$ in $R_{13}COOH$ wherein $R_{13}$ is $C_1$–$C_6$ alkyl at a temperature between 25° to 120° C., preferably at the reflux temperature of the reaction mixture. The compounds of formula III wherein $R_9$ is hydroxy may be prepared by reacting a compound of formula IV with chlorosulfonyl isocyanate in an appropriate solvent at temperature between –78° C. to 100° C., preferably at –20° C. to 60° C., followed by acid hydrolysis. The appropriate solvents include methylene chloride, dimethyl formamide, tetrahydrofuran, and toluene, preferably dimethyl formamide or methylene chloride. The above formed compounds wherein $R_9$ is hydrogen, $C_1$–$C_6$ alkyl or hydroxy may be heated in aqueous acid to give the compounds of formula III. The appropriate aqueous acids are 85% phosphoric acid, hydrochloric acid, sulfuric acid, or acetic acid, preferably 85% phosphoric acid. The reaction is generally carried out at about 25 to 150° C., preferably 80 to 130° C. Alternatively, the formed compounds may be heated with phosphorous pentoxide and N,N-dimethylcyclohexanamine at about 150 to 200° C.

The compounds of formula IV may be prepared by conventional methods.

The compounds of formula I wherein B is $CR_1R_2R_{11}$ or $CH_2A$, $(CH_2)_2A$ wherein A is as defined above with reference to formula I, and $R_3$ is hydrogen, $C_1$–$C_6$ alkyl, or hydroxy (hereafter $R_{14}$) may be prepared, as depicted in Scheme 1, by heating a compound of the formula VI, wherein $R_{14}$ is hydrogen, $C_1$–$C_6$ alkyl, or amino and $R_1$, $R_2$, $R_{11}$, $R_4$, $R_9$, and $R_6$ are as defined above, with ammonium chloride and $R_{14}CONH_2$ at reflux temperatures.

The compounds of formula I wherein B is $CR_1R_2R_{11}$ $CH_2A$, or $(CH_2)_2A$ wherein A is as defined above with reference to formula I and $R_3$ is as defined above other than hydrogen, $C_1$–$C_6$ alkyl, or hydroxy, may be prepared by reacting the 2-chloro derivatives of formula I wherein $R_3$ is chloro (formula I-B, not shown) with a nucleophile of formula $R_{15}H$ with or without an organic or inorganic base by the method described previously for the reaction with $R_{10}H$, wherein $R_{15}$ is $R_3$ other than hydrogen, $C_1$–$C_6$ alkyl, hydroxy, and chloro. The compounds of formula I-B may be prepared by a method analogous to that for the conversion of compounds III to compounds II.

The compounds of formula VI may be prepared, as shown in Scheme I, starting from compounds of the formula V by methods analogous to those for the conversion of compounds IV to compounds III.

The compounds of formula V may be prepared by methods analogous to the conventional methods used for the preparation of compounds of formula IV by using $YCOCH_2CN$ instead of malonitrile, wherein Y is $CR_1R_2R_{11}$, $CH_2A$ or $(CH_2)_2A$ wherein A is as defined above with reference to formula I.

Scheme 1

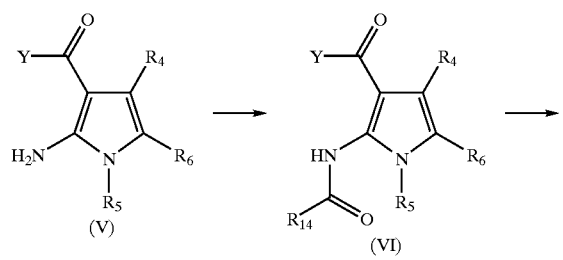

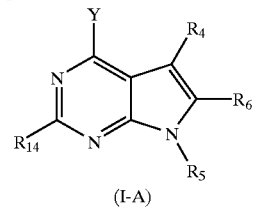

(I-A)

The acid addition salts of the compounds of formula I are prepared in a conventional manner by treating a solution or suspension of the free base of formula I with one chemical equivalent of a pharmaceutically acceptable acid. Conventional concentration or crystallization techniques are employed in isolating the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzene sulfonic, p-toluenesulfonic, mandelic, di-p-toluoyl-L-tartaric and related acids.

The novel compound of the invention of formula I may be administered alone or in combination with pharmaceutically acceptable carriers, in either single or multiple, e.g. up to three, doses. Suitable pharmaceutical carriers include inert solid diluents or fillers, sterile aqueous solution and various organic solvents. The pharmaceutical compositions formed by combining the novel compounds of formula I and the pharmaceutically acceptable carriers are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions of the novel compound of formula I in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

Additionally, it is possible to administer the compounds of the present invention topically when treating inflammatory conditions of the skin and this may be done by way of creams, jellies, gels, pastes and ointments in accordance with standard pharmaceutical practice.

The effective dosage for the compound of formula I depends on the intended route of administration and other factors such as age and weight of the patient, as generally known to a physician. The dosage also depends on the illness to be treated. The daily dosage will generally range from about 0.1 to 50 mg/kg of the body weight of the patient to be treated. For treatment of inflammatory diseases about 0.1 to about 100 mg/kg will be needed, for Alzheimer's disease, about 0.1 to about 50 mg/kg, as well as for gastrointestinal diseases, anorexia nervosa, hemorrhagic stress, drug and alcohol withdrawal symptoms, etc.

The methods for testing the compounds for formula I for their CRF antagonist activity are according to the procedures of Endocrinology, 116, 1653–1659 (1985) and Peptides, 10, 179–188 (1985) which determine the binding activity of a test compound to a CRF receptor. The binding activity for the compounds of formula I generally ranges from about 0.2 nanomolar to about 10 micromolar.

The following Examples illustrate the invention. The following abbreviations are used: Ph=phenyl, Me=methyl, Bu=butyl, Et=ethyl, Pr=propyl.

EXAMPLE 1

A. 2-amino-4-methyl-1-(2,4,6-trimethylphenyl) pyrrole-3-carbonitrile

A mixture 2-(2-bromo-1-methyl-ethyl idene)-malononitrile and 2,4,6-trimethylaniline (17.330 g, 91.24 mmol) in 40 mL of isopropanol was stirred at room temperature for 15 hours. The reaction mixture was concentrated to dryness and diluted with chloroform and water. The chloroform layer was neutralized with dilute sodium hydroxide and washed with brine, separated, dried and concentrated to give 33.000 g of brown oily solid. The solid was purified through silica gel column chromatography to give 9.35 g (47.5%) of the title compound as an orange-yellow solid. $^1$H NMR (CDCl$_3$) δ 2.0(s, 6H), 2.15(s, 3H), 2.35(s, 3H), 3.75(brs, 2H), 5.8(s, 1H), 6.95(s, 2H) ppm.

B. N-[3-cyano-4-methyl-1-(2,4,6-trimethylphenyl)-1H-pyrrol-2-yl]-acetamide

A mixture of the purified compound of step A (3.000 g, 12.54 mmol) and acetic anhydride (1.410 g, 1.31 ml, 13.82 mmol) in 3 ml of acetic acid was refluxed for 45 minutes, cooled and poured onto crushed ice and extracted with ethyl acetate. The organic layer was neutralized, dried and concentrated to give 3.71 g (105%) of dark-pink glass foam. $^1$H NMR (CDCl$_3$) □ 1.95(s, 6H), 2.2(s, 3H), 2.32 (s, 3H), 6.2(s, 1H), 6.8(brs, 1H, NH), 6.9(s, 2H) ppm.

C. 2,5-dimethyl-7-(2,4,6-trimethylphenyl)-3,7-dihydro-pyrrolo[2,3-d]pyrimidin-4-one A suspension of the compound of step B (3.200 g, 11.38 mmol) in 3 ml of 85% phosphoric acid was immersed in an oil bath preheated to 130° C. for 30 minutes. The reaction mixtures was cooled and poured onto crushed ice and stirred until solid formed and ice melted. The solid was filtered, washed with water to give a tan solid, the title compound, which was purified through silica gel column chromatography to give a tan solid. $^1$H NMR (CDCl$_3$) δ 1.92(s, 6H), 2.32(s, 3H), 2.41(s, 3H), 2.45(s, 3H), 2.46(s, 3H), 6.42(d, 1H), 6.95(s, 2H) ppm.

D. 4-chloro-2,5-dimethyl-7-(2,4,6-trimethylphenyl)-7H-pyrrolo-[2,3-d]pyrimidine A mixture of the compound of step C (1.030 g, 3.67 mmol) and POCl$_3$ (3 ml) was heated at reflux for 2.5 hours and cooled. The reaction mixture was poured into ice-water and extracted with ethyl acetate. The organic layer was washed with dilute sodium bicarbonate and brine, dried over anhydrous sodium sulfate, and concentrated to dryness to give the title compound as a tan solid which was purified through silica gel to give an off-white solid. $^1$H NMR (CDCl$_3$) δ 1.90(s, 6H), 2.35(s, 3H), 2.50(s, 3H), 2.65(s, 3H), 6.78(s, 1H), 7.00(s, 2H) ppm.

EXAMPLE 2

A. 2-amino-4,5-dimethyl-1-(2,4,6-trimethylphenyl)-1H-pyrrole-3-carbonitrile

A mixture of 3-hydroxy-2-butanone (100.000 g, 1.135 mol), 2,4,6-trimethylaniline (153.225 g, 1.135 mol) and p-toluenesulfonic acid (0.670 g) in 500 ml of benzene was refluxed using a Dean-Stark trap to remove water. After 2 hours, malononitrile (75.000 g, 1.135 mol) was added and the mixture was refluxed for an additional 10 hours until all of the starting material was consumed. The reaction mixture was cooled and precipitate formed and filtered. The solid was washed with a minimum amount of ethanol. The solid was diluted with 500 ml of benzene and product was dissolved. Some undesired product was insoluble and was filtered off. The filtrate was concentrated to give a tan solid which was recrystallized from ethanol to give 130.260 g of off-white crystals. $^1$H NMR (CDCl$_3$) δ 1.68(s, 3H), 1.93(s, 6H), 2.05(s, 3H), 2.31(s, 3H), 3.62(brs, 2H), 6.95(s, 2H) ppm.

B. N-[3-cyano-4,5-dimethyl-1-(2,4,6-trimethyphenyl)-1H-pyrrol-2-yl]-acetamide The title compound was prepared as a tan solid by the procedure analogous to that of Example 1A starting with the compound of step A and acetic anhydride in acetic acid. The crude material was pure and used directly for the next cyclization step. $^1$H NMR (CDCl$_3$) δ 1.75(s, 3H), 1.80(s, 6H), 1.95(s, 3H), 2.18(s, 3H), 2.30(s, 3H), 6.60(brs, 1H), 6.93(s, 2H) ppm.

C. 2,5,6-trimethyl-7-(2,4,6-trimethylphenyl)-3,7-dihydro-pyrrol[2,3-d]pyrimidin-4-one A mixture of the compound of step B(157.600 g, 0.53 mol) and 100 ml of 85% phosphoric acid was heated for 0.5 hours in an oil bath at a temperature of 130° C. All the starting material was consumed and the desired product formed. The mixture was cooled, poured into 1200 ml of ice-water, and stirred. Precipitate formed and was filtered. The solid was washed with water, dried overnight to give 113.220 g of the title compound as brick-pink solid. $^1$H NMR (CDCl$_3$) δ 1.85(s, 6H), 1.87(s, 3H), 2.34(s, 3H), 2.41(s, 3H), 2.44(s, 3H), 7.00(s, 2H) ppm.

EXAMPLE 3

A. 2-amino-4,5-diethyl-1-(2,4,6-trimethylphenyl)-1H-pyrrole-3-carbonitrile

The crude material of the title compound was prepared as an oil by the procedure analogous to that of Example 2A starting with 4-hydroxy-3-hexanone. The crude material was used directly for the next acetylation step without further purification.

B. N-[3cyano-4,5-diethyl-1-(2,4,6-trimethylphenyl)-1H-pyrrol-2-yl]-acetamide

The title compound was prepared as an oil by the procedure of Example 1A starting with the compound of above step A and acetic anhydride in acetic acid. The crude material was purified through silica gel column chromatography using chloroform as eluent to give the title compound as an oil. $^1$H NMR (CDCl$_3$) δ 0.85(t, 3H), 1.26(t, 3H), 1.92(s, 6H), 2.19(s, 3H), 2.23(q, 2H), 2.33(s, 3H), 2.59(q, 2H), 6.95(s, 2H) ppm.

C. 2-methyl-5,6-diethyl-7-(2,4,6-trimethylphenyl)-3,7-dihydro-pyrrolo[2,3-d]pyrimidin-4-one The title compound was prepared as a brown solid by the procedure of Example 2C starting with the compound of above step B and 85% phosphoric acid. The crude material was used directly for the next chlorination reaction without further purification.

EXAMPLE 4

The following compounds were prepared according to the method of Example 1 starting from the corresponding 2,5,6-trialkyl-7-(2,4,6-trimethylphenyl)-3,7-dihydro-pyrrolo[2,3-d]pyrimidin-4-one.

4-chloro-2,5,6-trimethyl-7-(2,4,6-trimethylphenyl)-7H-pyrrolo[2,3-d]pyrimidine—a tan solid. $^1$H NMR (CDCl$_3$) δ 1.81(s, 6H), 1.99(s, 3H), 2.35(s, 3H), 2.46(s, 3H), 2.59(s, 3H), 7.01 (s, 2H) ppm.

4-chloro-2-methyl-5,6-diethyl-7-(2,4,6-trimethyllhenyl)-7H-yrrolo[2,3]pyrimidine—a tan solid. 1H NMR (CDCl$_3$) δ 0.96(t, 3H), 1.31(t, 3H), 1.85(s, 6H), 2.38(s, 3H), 2.46(q, 2H), 2.62(s, 3H), 2.62(s, 2H), 2.92(q, 2H), 7.02(s, 2H) ppm.

EXAMPLE 5

Butyl-ethyl-[2,5-dimethyl-7-(2,4,6-trimethylphenyl)-7H-pyrrolo[2,3-d]pyrimidin-4-yl]amine A mixture of 4-chloro-2,5-dimethyl-7-(2,4,6-trimethylphenyl)-7H-pyrrolo[2,3-d]pyrimidine (1.000 g, 3.36 mmol) and N-ethylbutylamine (3.400 g, 33.60 mmol) in 5 ml of dimethylsulfoxide was heated to reflux for 1.5 hours. The mixture was cooled and treated with water and a few drops of 2 N HCl to pH 6.5 and extracted with ethyl acetate. The organic layer was separated, washed with dilute sodium bicarbonate, brine, and dried over sodium sulfate anhydrous and concentrated to dryness. The residue was purified through silica gel column chromatography to give 995 mg (81% yield) of the title compound as an oil. $^1$H NMR (CDCl$_3$) δ 6 0.90 (t, 3H), 1.23(t, 3H), 1.35(m, 2H), 1.60–1.70(m, 2H), 1.92(s, 6H), 2.30(s, 3H), 2.40(s, 3H), 2.46(s, 3H), 3.58(t, 2H), 3.66(q, 2H), 6.55(s, 1H), 6.95(s, 2H) ppm. The corresponding hydrogen chloride salt was prepared as a white crystals after recrystallization from ethyl acetate. $^1$H NMR (D$_2$O) δ 0.90(t, 3H), 1.34(m, 5H), 1.75(m, 2H), 1.90(s, 6H), 2.37(s, 3H), 2.48(s, 3H), 2.55(s, 3H), 3.80–3.94(m, 4H), 7.09(s, 2H) ppm.

EXAMPLE 6

The following compounds were prepared starting with the appropriate amine and the appropriate 4-chloro-2,5,6-trialkyl-7-(substituted phenyl)-7H-pyrrolo[2,3-d]pyrimidine and employing the general procedure of Example 5.

(A)

| B | R$_3$ | R$_4$ | R$_6$ | $^1$H NMR(CDCl$_3$) δ (ppm) |
|---|---|---|---|---|
| NMe$_2$ | Me | Me | Me | 1.82(s, 6H), 2.00(s, 3H) 2.38(s, 3H) 2.40(s, 3H) 2.90(s, 3H), 3.58(s, 6H), 7.03(s, 2H) |
| NEt2 | Me | Me | Me | 1.22(t, 6H), 1.84(s, 6H), 1.94(s, 3H), 2.35(s, 3H), 2.38(s, 3H), 2.55(s, 3H), 3.60(q, 4H), 6.98(s, 2H) |
| N(n-Pr)$_2$ | Me | Me | Me | 0.90(t, 6H), 1.68(q, 4H), 1.85(s, 6H), 1.95(s, 3H), 2.35(s, 3H), 2.39(s, 3H), 2.48(s, 3H), 3.53(q, 4H), 6.99(s, 2H) |
| N-(n-Bu)$_2$ | Me | Me | Me | 0.88(t, 6H), 1.30(m, 4H), 1.61(m, 4H), 1.82(s, 6H), 1.92(s, 3H), 2.30(s, 3H), 2.34(s, 3H), 2.47(s, 3H), 3.50(t, 4H), 6.95(s, 2H) |
| EtN(n-Pr) | Me | Me | Me | 0.92(t, 3H), 1.20(t, 3H), 1.64(m, 2H), 1.85(s, 6H), 1.94(s, 3H), 2.35(s, 3H), 2.38(s, 3H), 2.47(s, 3H), 3.49(t, 2H), 3.59(q, 2H), 6.99(s, 2H) |
| EtN(n-Bu) | Me | Me | Me | 0.90(t, 3H), 1.19(t, 3H), 1.33(m, 2H), 1.60(m, 2H), 1.83(s, 6H), 1.92(s, 3H), 2.33(s, 3H), 2.35(s, 3H), 2.45(s, 3H), 3.51(t, 2H), 3.58(q, 2H), 6.96(s, 2H) |
| EtN(CH$_2$)$_2$OH | Me | Me | Me | 1.25(t, 3H), 1.78(s, 6H), 1.90(s, 3H), 2.30(s, 3H), 2.36(s, 3H), 2.40(s, 3H), 3.64(q, 2H), 3.75(m, 2H), 3.86(t, 2H), 6.96(s, 2H) |
| (n-Bu)N(CH$_2$)$_2$OH | Me | Me | Me | 0.95(t, 3H), 1.35(m, 2H), 1.71(m, 2H), 1.81(s, 6H), 1.92(s, 3H), 2.31(s, 3H), 2.37(s, 3H), 2.44(s, 3H), 3.55(dd, 2H), 3.72(t, 2H), 3.87(t, 2H), 6.95(s, 2H) |
| MeN(CH$_2$CHMe$_2$) | Me | Me | Me | 0.89(s, 3H), 0.91(s, 3H), 1.81(s, 6H), 1.91(s, 3H), 1.96–2.10(m, 1H), 2.32(s, 3H), 2.35(s, 3H), 2.43(s, 3H), 3.11(s, 3H), 3.32(d, 2H), 6.95(s, 2H) |
| ▷―N(n-Pr) | Me | Me | Me | 0.35(dd, 2H), 0.47(m, 2H), 0.90(t, 3H), 1.10(m, 1H), 1.67(m, 2H), 1.83(s, 6H), 1.93(s, 3H), 2.33(s, 3H), 2.37(s, 3H), 2.45(s, 3H), 3.41(d, 2H), 3.62(t, 2H), 6.97(s, 2H) |

-continued

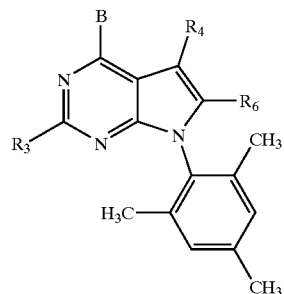
(A)

| B | R₃ | R₄ | R₆ | $^1$H NMR(CDCl$_3$) δ (ppm) |
|---|---|---|---|---|
| N(CH$_2$CH=CH$_2$)$_2$ | Me | Me | Me | 1.85(s, 6H), 1.96(s, 3H), 2.36(s, 3H), 2.39(s, 3H), 2.49(s, 3H), 4.18(d, 4H), 5.20–5.32(m, 4H), 5.90–6.10(m, 2H), 7.00(s, 2H) |
| MeN—CHMe(Et) | Me | Me | Me | 0.87(t, 3H), 1.29(d, 3H), 1.4–1.8(m, 3H), 1.82(s, 3H), 1.86(s, 3H), 1.95(s, 3H), 2.35(s, 3H), 2.37(s, 3H), 2.47(s, 3H), 3.02(s, 3H), 4.34(m, 1H), 6.99(s, 2H) |
| N(CH$_2$CH$_2$OH)$_2$ | Me | Me | Me | 1.59(brs, 2H), 1.81(s, 6H), 1.94(s, 3H), 2.34(s, 3H), 2.39(s, 3H), 3.80–3.95(m, 8H), 6.98(s, 2H) |
| HO(CH$_2$)$_3$N(CH$_2$)$_2$OH | Me | Me | Me | 1.80(s, 6H), 1.93(s, 3H), 1.90–2.00(m, 2H), 2.33(s, 3H), 2.39(s, 3H), 2.43(s, 3H), 3.65(t, 2H), 3.70–3.85(m, 2H), 3.89(m, 2H), 6.98(s, 2H) |
| (n-Bu)N(CH$_2$CH$_2$OMe) | Me | Me | H | 0.91(t, 3H), 1.31(m, 2H), 1.67(m, 2H), 1.90(s, 6H), 2.32(s, 3H), 2.41(s, 3H), 2.42(s, 3H), 3.36(s, 3H), 3.60–3.70(m, 4H), 3.82(t, 2H), 6.56(s, 1H), 6.95(s, 2H) |
| p-Me-PhCH$_2$N(CH$_2$)$_3$OH | Me | Me | H | 1.80(m, 2H), 1.90(s, 6H), 2.20(s, 3H), 2.30(s, 3H), 2.34(s, 3H), 2.49(s, 3H), 3.54(t, 2H), 3.82(t, 2H), 4.90(s, 2H), 6.58(s, 1H), 6.95(s, 2H), 7.10–7.25(m, 4H) |
| EtN(n-Pr) | Me | Et | Et | 0.93(t, 6H), 1.1–1.3(m, 6H), 1.68(m, 2H), 1.88(s, 6H), 2.36(s, 3H), 2.42(q, 2H), 2.49(s, 3H), 2.80(q, 2H), 3.49(t, 2H), 3.58(q, 2H), 6.99(s, 2H) |
| EtN(n-Bu) | H | Me | Me | 0.91(t, 3H), 1.23(t, 3H), 1.30(m, 2H), 1.62(m, 2H), 1.89(s, 6H), 2.30(s, 3H), 2.44(s, 3H), 3.58(t, 2H), 3.65(q, 2H), 6.67(s, 1H), 6.95(s, 2H), 8.29(s, 1H) |
| EtN(n-Pr) (HCl salt) | Me | Me | H | 0.93(t, 3H), 1.25(t, 3H), 1.70(m, 2H), 1.91(s, 6H), 2.33(s, 3H), 2.42(s, 3H), 3.55(m, 2H), 3.69(m, 2H), 6.58(s, 1H), 6.96(s, 2H) |
| N(n-Pr)$_2$ | Me | Me | H | 0.90(t, 6H), 1.65(m, 4H), 1.90(s, 6H), 2.30(s, 3H), 2.40(s, 3H), 2.45(s, 3H), 3.5–3.6(m, 4H), 6.55(s, 1H), 6.93(s, 2H) |
| N(CH$_2$CH=CH$_2$)$_2$ | Me | Me | H | 1.90(s, 6H), 2.30(s, 3H), 2.40(s, 3H), 2.48(s, 3H), |

-continued

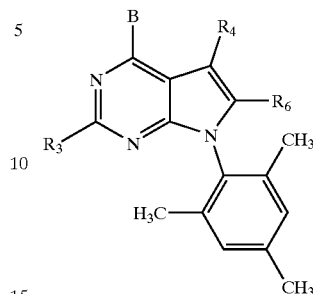
(A)

| B | R₃ | R₄ | R₆ | $^1$H NMR(CDCl$_3$) δ (ppm) |
|---|---|---|---|---|
| | | | | 4.20(d, 4H), 5.15–5.30(m, 4H), 5.09–6.10(m, 2H), 6.55(s, 1H), 6.95(s, 2H) |
| EtN(CH$_2$CH(CH$_3$)$_2$) | Me | Me | H | 0.95(t, 3H), 1.23(t, 3H), 1.95(s, 6H), 2.11(m, 1H), 2.35(s, 3H), 2.46(s, 3H), 2.50(s, 3H), 3.44(d, 2H), 3.68(q, 2H), 6.59(s, 1H), 6.98(s, 2H) |
| EtN(CH$_2$C(Me)=CH$_2$) | Me | Me | H | 1.21(t, 3H), 1.73(d, 3H), 1.93(s, 6H), 2.34(s, 3H), 2.42(s, 3H), 2.48(s, 3H), 3.63(q, 2H), 4.18(s, 2H), 4.95(s, 1H), 5.05(s, 1H), 6.58(s, 1H), 6.97(s, 2H) |
| EtN(CH$_2$)$_2$N(CH$_3$)$_2$ | Me | Me | H | 1.26(t, 3H), 1.88(s, 6H), 2.31(s, 3H), 2.34(s, 6H), 2.41(s, 3H), 2.43(s, 3H), 2.62(m, 2H), 3.64(q, 2H), 3.74(m, 2H), 6.55(s, 1H), 6.94(s, 2H) |
| EtN(CH$_2$C(Me)$_2$) | Me | Me | Me | 0.91(d, 6H), 1.17(t, 3H), 1.84(s, 6H), 1.95(s, 3H), 2.05(m, 1H), 2.35(s, 3H), 2.38(s, 3H), 2.47(s, 3H), 3.36(d, 2H), 3.61(q, 2H), 6.98(s, 2H) |
| NH—CHEt$_2$ | Me | Me | Me | 0.96(t, 6H), 1.5–1.8(m, 4H), 1.82(s, 6H), 1.87(s, 3H), 2.3(s, 3H), 2.39(s, 3H), 2.40(s, 3H), 4.30(m, 1H), 4.76(d, 1H, NH), 6.94(s, 2H) |
| NH—CHEt$_2$ | Me | Me | H | 0.98(t, 6H), 1.5–1.8(m, 4H), 1.92(s, 6H), 2.32(s, 3H), 2.45(s, 3H), 2.46(s, 3H), 4.32(m, 1H), 4.82(d, 1H, NH), 6.44(s, 1H), 6.95(s, 2H) |
| NHCH(n-Pr)$_2$ | Me | Me | Me | 0.94(s, 6H), 1.3–1.7(m, 4H), 1.84(s, 6H), 1.89(s, 3H), 2.32(s, 3H), 2.39(s, 3H), 2.41(s, 3H), 4.46(s, 1H), 4.73(s, 1H, NH), 6.96(s, 2H) |
| NHCH(Me)(n-Bu) | Me | Me | Me | 0.92(t, 3H), 1.27(d, 3H), 1.37(m, 4H), 1.5–1.7(m, 2H), 1.83(s, 6H), 1.84(s, 3H), 1.89(s, 3H), 2.33(s, 3H), 2.40(s, 3H), 2.43(s, 3H), 4.41(m, 1H), 4.77(d, 1H, NH), 6.96(s, 2H) |
| NH(n-Bu) | Me | Me | H | 0.98(t, 3H), 1.35–1.45(m, 2H), 1.5–1.7(m, 2H), 1.90(s, 6H), 2.30(s, 3H), 2.43(s, 3H), 2.44(s, 3H), 3.57(q, 2H), 4.90(m, t, 1H, NH), 6.38(s, 1H), 6.93(s, 2H) |

-continued

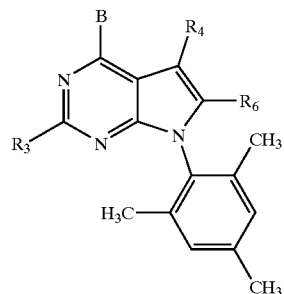

(A)

| B | R₃ | R₄ | R₆ | ¹H NMR(CDCl₃) δ (ppm) |
|---|---|---|---|---|
| NHEt | Me | Me | H | 1.30(t, 3H), 1.90(s, 6H), 2.30(s, 3H), 2.44(s, 3H), 2.46(s, 3H), 3.62(m, 2H), 4.90(t,1H, NH), 6.40(s, 1H), 6.93(s, 2H) |
| NH-cyclopropyl | Me | Me | Me | 0.57(m, 2H), 0.85(m, 2H), 1.81(s, 6H), 1.87(s, 3H), 2.31(s, 3H), 2.34(s, 3H), 2.48(s, 3H), 3.00(m, 1H), 5.17(s, 1H), 6.95(s, 2H) |
| NH-(R)-CH(Et)(CH₂OH) | Me | Me | Me | 1.05(t, 3H), 1.5–1.8(m, 2H), 1.80(s, 6H), 1.89(s, 3H), 2.31(s, 3H), 2.40(s, 6H), 3.84(2 sets of ABq, 2H), 3.96(m, 1H), 5.14(d, 1H, NH), 6.95(s, 2H), 7.04 (s, 1H) |
| NHCH(Me)(Et) | Me | Me | Me | 0.99(t, 3H), 1.25(d, 3H), 1.57(m, 2H), 1.82(s, 6H), 1.88(s, 3H), 2.31(s, 3H), 2.39(s, 3H), 2.41(s, 3H), 4.35(m, 1H), 4.78(d, 1H, NH), 6.94(s, 2H) |
| NH-(S)-CH(Et)(CH₂OH) | Me | Me | Me | 1.05(t, 3H), 1.5–1.8(m, 2H), 1.80(s, 6H), 1.89(s, 3H), 2.31(s, 3H), 2.40(s, 6H), 3.84(2 sets of ABq, 2H), 3.96(m, 1H), 5.14(d, 1H, NH), 6.95(s, 2H), 7.04 (s, 1H) |
| NH-cyclopentyl | Me | Me | Me | 1.49(m, 2H), 1.67(m, 2H), 1.81(s, 6H), 1.87(s, 3H), 2.13(m, 2H), 2.31(s, 3H), 2.37(s, 3H), 2.42(s, 3H), 4.58(m, 1H), 4.93(d, 1H, NH), 6.94(s, 2H) |
| NH-(S)-CH(Et)(CH₂OH) | Me | Me | H | 1.08(t, 3H), 1.5–1.8(m, 2H), 1.89(s, 6H), 2.30(s, 3H), 2.43(s, 3H), 2.448(s, 3H), 2.453(s, 3H), 3.86(2 sts of ABq, 2H), 3.98(m, 1H), 5.17(d, 1H, NH), 6.48 (s, 1H), 6.81(s, 1H), 6.94 (s, 1H) |
| NH-(S)-CH(Et)(CH₂OMe) | Me | Me | H | 0.98(t, 3H), 1.6–1.8(m, 2H), 1.90(s, 3H), 1.91(s, 3H), 2.30(s, 3H), 2.42(s, 3H), 2.44(s, 3H), 3.39(s, 3H), 3.53(2 sets of ABq, 2H), 4.46(m, 1H), 5.24(d, 1H, NH), 6.42(s, 1H), 6.92 (s, 2H) |
| NHCH(Me)(Et) | Me | Me | H | 0.99(t, 3H), 1.26(d, 3H), 1.5–1.7(m, 2H), 1.91(s, 6H), 2.30(s, 3H), 2.44(s, 6H), 4.34(m, 1H), 4.79(d, 1H, NH), 6.42(s, 1H), 6.93 (s, 2H) |
| NH-(R)-CH(Et)(CH₂OMe) | Me | Me | Me | 1.00(t, 3H), 1.55–1.8(m, 2H), 1.82(s, 6H), 1.87(s, |

-continued

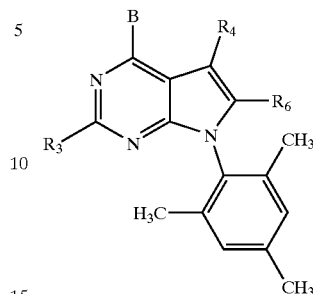

(A)

| B | R₃ | R₄ | R₆ | ¹H NMR(CDCl₃) δ (ppm) |
|---|---|---|---|---|
| | | | | 3H), 2.31(s, 3H), 2.38(s, 3H), 2.39(s, 3H), 3.39(s, 3H), 3.54(m, 2H), 4.45(m, 1H), 5.25(d, 1H, NH), 6.94 (s, 2H) |
| NH-(S)-CH(Et)(CH₂OMe) | Me | Me | Me | 1.00(t, 3H), 1.55–1.8(m, 2H), 1.82(s, 6H), 1.87(s, 3H), 2.31(s, 3H), 2.38(s, 3H), 2.39(s, 3H), 3.39(s, 3H), 3.54(m, 2H), 4.45(m, 1H), 5.25(d, 1H, NH), 6.94 (s, 2H) |
| NH—CH₂CH(Me)(Et) | Me | Me | Me | 0.96(t, 3H), 1.00(d, 3H), 1.1–1.3(m, 2H), 1.4–1.6(m, 2H), 1.6–1.8(m, 1H), 1.82 (s, 6H), 1.88(s, 3H), 2.31(s, 3H), 2.39(s, 3H), 2.42(s, 3H), 3.40(m, 1H), 3.54(m, 1H), 5.00(t, 1H, NH), 6.94 (s, 2H) |
| NH-(S)-CH(CH₂Ph)(CH₂OH) | Me | Me | Me | 1.77(s, 3H), 1.78(s, 3H), 1.82(s, 3H), 1.99(s, 3H), 2.30(s, 3H), 2.41(s, 3H), 2.84(m, 1H), 3.12(m, 1H), 3.75(m, 1H), 3.93(m, 1H), 4.27(m, 1H), 5.15(d, 1H, NH), 6.94(s, 2H), 7.2–7.4 (m, 5H) |
| NH-(R)-CH(CH₂Ph)(CH₂OH) | Me | Me | Me | 1.77(s, 3H), 1.78(s, 3H), 1.82(s, 3H), 1.99(s, 3H), 2.30(s, 3H), 2.41(s, 3H), 2.84(m, 1H), 3.12(m, 1H), 3.75(m, 1H), 3.93(m, 1H), 4.27(m, 1H), 5.15(d, 1H, NH), 6.94(s, 2H), 7.2–7.4 (m, 5H) |
| NH-(S)-CH(CH₂Ph)-(CH₂OMe) | Me | Me | Me | 1.80(s, 3H), 1.83(s, 3H), 1.88(s, 3H), 2.31(s, 3H), 2.33(s, 3H), 2.44(s, 3H), 2.90(m, 1H), 3.13(m, 1H), 3.40(s, 3H), 3.44(m, 2H0, 4.70(m, 1H), 5.35(d, 1H, NH), 6.95(s, 2H0), 7.2–7.4(m, 5H) |
| NH-(R)-CH(CH₂Ph)-(CH₂OMe) | Me | Me | Me | 1.80(s, 3H), 1.83(s, 3H), 1.88(s, 3H), 2.31(s, 3H), 2.33(s, 3H), 2.44(s, 3H), 2.90(m, 1H), 3.13(m, 1H), 3.40(s, 3H), 3.44(m, 2H0, 4.70(m, 1H), 5.35(d, 1H, NH), 6.95(s, 2H0), 7.2–7.4(m, 5H) |
| NH-(S)-CH(Et)(CH₂OEt) | Me | Me | H | 1.00(t, 3H), 1.20(t, 3H), 1.6–1.8(m, 2H0), 1.90(s, 3H), 1.91(s, 3H), 2.30(s, 3H), 2.42(s, 3H), 2.43(s, 3H), 3.4–3.6(m, 2H), 4.41 (m, 1H), 5.34(d, 1H, NH), 6.42(s, 1H), 6.93(s, 2H) |

-continued (A)

[Structure: pyrrolo[2,3-d]pyrimidine with B at 4-position, R4 at 5, R6 at 6, R3 at 2, and N-substituted with 2,4,6-trimethylphenyl (mesityl) group]

| B | R₃ | R₄ | R₆ | ¹H NMR(CDCl₃) δ (ppm) |
|---|---|---|---|---|
| NHCH₂CH(n-Bu)(Et) | Me | Me | Me | 0.89(t, 3H), 0.95(t, 3H), 1.2–1.4(m, 7H), 1.54–1.62(m, 1H), 1.82(s, 6H), 1.88(s, 3H), 2.31(s, 3H), 2.39(s, 3H), 2.42(s, 3H), 3.53(m, 2H), 4.90(m, 1H), 6.95(s, 2H) |

(B)

[Structure: pyrrolo[2,3-d]pyrimidine with NR₁R₂ at 4-position, R₄ at 5, R₆ at 6, H₃C at 2, R₅ on N]

| NR₁R₂ | R₄ | R₆ | R₅ |
|---|---|---|---|
| | ¹H-NMR(CDCl₃) δ (ppm) | | |
| EtN(n-Bu) | Me | Me | 2,4-dimethylphenyl |
| | 0.89(t, 3H), 1.15(t, 3H), 1.30(m, 2H), 1.2–1.4(m, 2H), 1.87(s, 3H), 1.97(s, 3H), 2.33(s, 3H), 2.37(s, 3H), 2.44(s, 3H), 3.49(t, 2H), 3.55(q, 2H), 6.9–7.2(m, 3H) | | |
| N(n-Pr)₂ | Me | Me | 2,4-dimethylphenyl |
| | 0.86(t, 6H), 1.62(m, 4H), 1.87(s, 3H), 1.97(s, 3H), 2.34(s, 3H), 2.37(s, 3H), 3.48(m, 4H), 6.95–7.20(m, 3H) | | |
| EtN(n-Bu) | Me | Me | 2,6-dimethylphenyl |
| | 0.89(t, 3H), 1.31(t, 3H), 1.31(m, 2H), 1.62(m, 2H), 1.86(s, 3H), 1.90(s, 3H), 2.35(s, 3H), 2.43(s, 3H), 3.50(t, 2H), 3.56(q, 2H), 7.1–7.2(m, 3H) | | |
| EtN(n-Pr) | Me | Me | 2,4-dimethylphenyl |
| | 0.89(t, 3H), 1.18(t, 3H), 1.66(m, 2H), 1.86(s, 6H), 1.91(s, 3H), 2.35(s, 3H), 2.43(s, 3H), 3.43(m, 2H), 3.56(m, 2H), 7.0–7.2(m, 3H) | | |
| EtN(n-Bu) | Me | H | 2,5-dimethylphenyl |
| | 0.93(t, 3H), 1.22(t, 3H), 1.25–1.45(m, 2H), 1.6–1.8(m, 2H), 2.04(s, 6H), 2.33(s, 3H), 2.41(s, 3H), 2.42(s, 3H), 3.58(t, 2H), 3.64(q, 2H), 6.70(s, 1H), 7.06(s, 1H), 7.1–7.25(m, 2H) | | |
| EtN(n-Bu) | Me | H | 3-methyl-4-chlorophenyl |
| | 0.94(t, 3H), 1.23(t, 3H), 1.23–1.45(m, 2H), 1.4–1.6(m, 2H), 2.43(s, 3H), 2.44(s, 3H), 2.58(s, 3H), 3.4–3.75(m, 4H), 6.94(s, 1H), 7.4–7.65(m, 3H) | | |
| EtN(n-Bu) | Me | H | 2,6-dimethyl-4-bromophenyl |
| | 0.92(t, 3H), 1.22(t, 3H), 1.25–1.40(m, 2H), 1.55–1.60(m, 2H), 1.91(s, 6H), 2.40(s, 3H), 2.43(s, 3H), 3.57(m, 2H), 3.64(q, 2H), 6.50(s, 1H), 7.27(s, 2H) | | |
| EtN(n-Bu) | Me | H | 2,4-dimethyl-6-bromophenyl |
| | 0.98(t, 3H), 1.28(T, 3H), 1.3–1.5(m, 2H), 1.6–1.8(M, 2H), 2.00(s, 3H), 2.36(s, 3H), 2.48(s, 3H), 2.53(s, 3H), 3.64(t, 2H), 3.71(q, 2H), 6.63(s, 1H), 7.09(d, 1H), 7.38(d, 1H) | | |
| NHCH(Et)₂ | Me | H | 2,6-dimethyl-4-bromophenyl |
| | 0.98(t, 6H), 1.5–1.8(m, 4H), 1.94(s, 6H), 2.44(s, 3H), 2.45(s, 3H), 4.30(M, 1H), 4.80(d, 1H, NH), 6.39(s, 1H), 7.28(s, 2H) | | |
| NHCH(Et)(CH₂OH) | Me | H | 2,6-dimethyl-4-bromophenyl |
| | 1.07(t, 3H), 1.5–1.8(m, 2H), 1.90(s, 6H), 2.42(s, 3H), 2.44(s, 3H), 3.5–3.8(m, 2H), 3.87(m, 1H), 5.18(d, 1H, NH), 6.45(s, 1H), 6.56(s, 1H), 7.27(s, 1H) | | |
| NHCH(Et)(CH₂Ome) | Me | H | 2,6-dimethyl-4-bromophenyl |
| | 1.00(t, 3H), 1.55–1.75(m, 2H), 1.92(s, 6H), 2.42(s, 3H), 2.43(s, 3H), 3.39(s, 3H), 3.55 (2 sets of ABq, 2H), 4.46(m, 1H), 5.28(d, 1H, NH), 6.38(s, 1H), 7.26(s, 2H) | | |

EXAMPLE 7

A. 1-[2-Amino-4,5-dimethyl-1-(2,4,6-trimethylphenyl)-1H-pyrrol-3-yl]-2-ethyl-butan-1-one A mixture of 3-hydroxy-2-butanone (0.637 g, 7.23 mmol), 2,4,6-trimethylaniline (0.973 g, 7.19 mmol) and p-toluenesulfonic acid (0.012 g, 0.06 mmol) in 15 ml of benzene was refluxed using a Dean-Stark trap to remove water. After 3 hours, 4-ethyl-3-oxo-hexanenitrile (1.008 g, 0.724 mmol) was added and the mixture was refluxed for an additional 15 hours until all the starting material was consumed. The mixture was cooled to room temperature, diluted with water, and extracted with ethyl acetate. The organic layer was dried and concentrated to give 1.679 g of brown oil which was purified by silica gel column chromatography to give 368 mg of the title compound as a brown oil and 732 mg of undesired 2-(2-ethyl-butyl)-4,5-dimethyl-1-(2,4,6-trimethylphenyl)-1H-pyrrole-3-carbonitrile as a yellow solid. ¹H-NMR (CDCl₃) (the title compound) δ 0.94(t, 6H), 1.4–1.8(m, 4H), 1.73(s, 3H), 1.98(s, 6H), 2.25(s, 3H), 2.34(s, 3H), 3.00(m, 1H), 5.80(brs, 2H), 6.99(s, 2H) ppm ¹H-NMR (CDCl₃) (2-(2-ethyl-butyl)-4,5-dimethyl-1-(2,4,6-trimethylphenyl)-1H-pyrrole-3-carbonitrile) δ 0.85(t, 6H), 1.5–1.85(m, 4H), 1.71(s, 3H), 1.88(s, 6H), 1.95–2.10 (m, 1H), 2.14(s, 3H), 234Hs, 3H), 6.96(s, 2H) ppm.

B. N-[3-(2-ethyl-butyryl)-4,5-dimethyl-1-(2,4,6-trimethylphenyl)-1H-DVrrol-2-yl]-acetamide A mixture of 1-[2-amino-4,5-dimethyl-1-(2,4,6-trimethylphenyl)-1H-pyrrol-3-yl]-2-ethyl-butan-1-one (326 mg, 1 mmol) and acetic anhydride (108 mg, 1.05 mmol) in 3 ml of acetic acid was heated to reflux for 2 hours. The mixture was cooled, quenched with water, neutralized with saturated potassium carbonate, and extracted with ethyl acetate. The organic layer was washed with brine, dried, and concentrated to give the title compound as a dark oil. The oil was purified through silica gel column chromatography to give 107 mg of the title compound as a brown oil. ¹H-NMR (CDCl₃) δ 6 0.88(t, 6H), 1.4–1.8(m, 4H), 1.76(s, 3H), 1.88(s, 3H), 1.93(s, 6H), 2.25(s, 3H), 2.28(s, 3H), 2.98(m, 1H), 6.89(s, 2H)ppu.

C. 4-(1-Ethyl-propyl)-2,5,6-trimethyl-7-(2,4,6-trimethylphenyl)-7H-pyrrolo[2,3-d]-pyrimidine A mixture of N-[3-(2-ethyl-butyl )4,5-dimethyl-1-(2,4,6-trimethylphenyl)-1H-pyrrol-2-yl]-acetamide (100 mg, 0.27 mmol), ammonium chloride (290 mg, 5.42 mmol), and acetamide (1.635 g) was heated to reflux for 2 hours. The mixture was cooled, quenched with water and extracted with ethyl acetate. The organic layer was dried and concentrated to give 56 mg of the title compound as a dark oil. The oil was purified through silica gel column chromatography to give the title compound as a yellow oil. ¹H-NMR (CDCl₃) δ 0.85(t, 6H), 1.70–2.0(m, 4H), 1.83(s, 6H), 1.99(s, 3H), 2.36(s, 3H), 2.44(s, 3H), 2.61 (s, 3H), 3.26(m, 1H), 7.00(s, 2H) ppm.

EXAMPLE 8

4-[4-(Butyl-ethyl-amino)-2,5-dimethyl-pyrrolo[2,3-d]pyrimidin-7-yl]-3,5-dimethyl-benzoic acid A mixture of 7-(4-bromo-2,6-dimethyl-phenyl)-2,5-dimethyl-7H-pyrrolo[2,3-d]pyrimidine-4-yl]-butyl-ethyl-amine (0.700 g, 1.63 mmol) in 11 ml of dry tetrahydrofuran (THF) was treated with n-butyl lithium (n-BuLi) (2.5 M in hexane, 1.79 mmol) at −78° C. and stirred at that temperature for 30 minutes.

The solution was quenched with an excess of water and extracted with ethyl acetate, dried and concentrated to give 0.041 9 (78%) of butyl-ethyl-[2,5-dimethyl-7-(2,6-dimethylphenyl)-7H-pyrrolo[2,3-d]pyrimidine-4-yl]amine as a clear oil. The oil was treated with 1 N HCl in methanol and concentrated to dryness. The residue was recrystallized from ethyl acetate to give the corresponding HCl salt as white crystals, mp 148–150° C.

The rest of the reaction mixture was quenched with an excess of dry ice at −78° C. and the −78° C. bath was removed. After 30 minutes, tlc showed that no starting material was left, and the mixture was quenched with water and extracted with ethyl acetate. The organic layer was washed with brine, dried and concentrated to give an off-white solid (0.550 g). The solid was recrystallized from 2-propanol to give the title compound as white crystals, mp 228–230° C.

EXAMPLE 9

The following compounds were prepared by reacting an appropriate electrophile and an appropriate carbanion which was generated from the halogen/metal exchange of an appropriate 4-alkyl-/or 4-dialkyl-amino-2,5-dimethyl-7-(2,6-dimethyl-4-bromophenyl)-/or 2-bromo-4,6-dimethylphenyl)-7H-pyrrolo[2,3-d]pyrimidine with n-BuLi in dry THF at −78° C. as described in the Example 8.

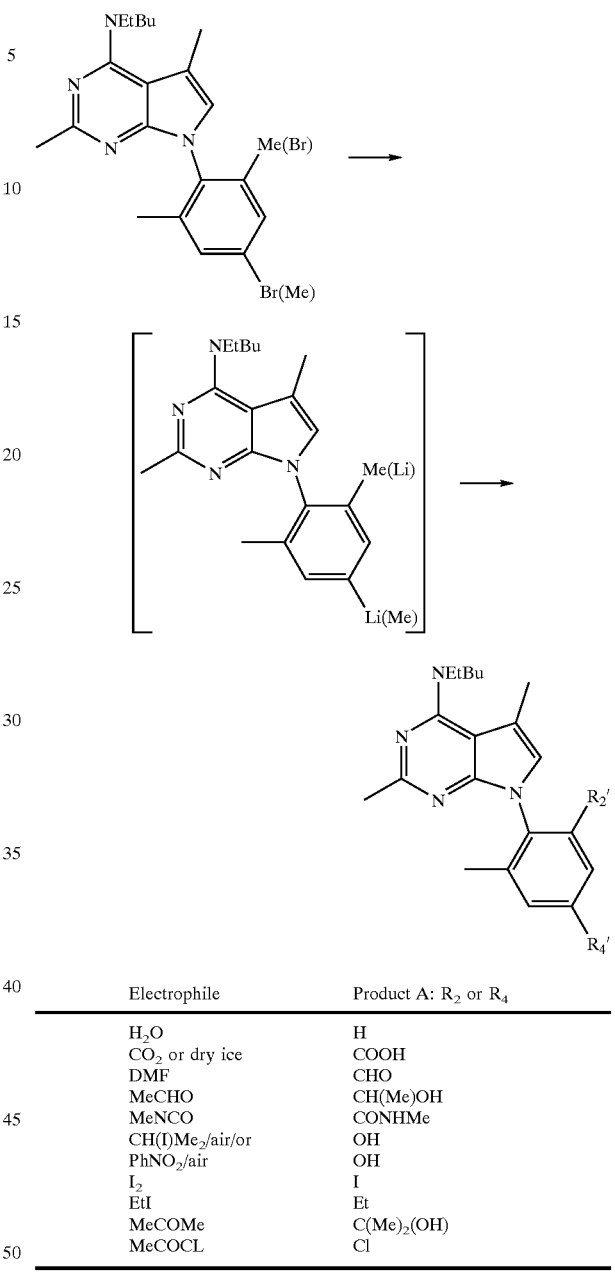

| Electrophile | Product A: R₂ or R₄ |
|---|---|
| H₂O | H |
| CO₂ or dry ice | COOH |
| DMF | CHO |
| MeCHO | CH(Me)OH |
| MeNCO | CONHMe |
| CH(I)Me₂/air/or | OH |
| PhNO₂/air | OH |
| I₂ | I |
| EtI | Et |
| MeCOMe | C(Me)₂(OH) |
| MeCOCL | Cl |

EXAMPLE 10

[4(Butyl-ethyl-amino)-2,5-dimethyl-pyrrolo[2,3-d]pyrimidin-7-yl]-3,5-dimethyl-benzoic acid methyl ester A mixture of 4-[4-(butyl-ethyl-amino)-2,5-dimethyl-pyrrolo[2,3-d]pyrimidin-7-yl]-3,5-dimethyl-benzoic acid (0.230 g, 0.583 mmol) in 40 ml of 1 N HCl and methanol was heated at reflux for 3 hours (tlc showed that all starting materials were consumed). The mixture was concentrated to dryness. The residue was diluted with water and extracted with ethyl acetate. The organic layer was washed with saturated sodium bicarbonate, brine, dried and concentrated to give the title compound as a light brown oil. The oil was purified through silica gel column chromatography using 5% ethyl acetate in hexane as an eluent to give a golden oil. The corresponding HCl salt was prepared as an off-white solid, mp 58–60° C.

EXAMPLE 11

[4-(Butyl-ethyl-amino)-2,5-dimethyl-pyrrolo[2,3-d]pyrimidin-7-yl]-3,5-dimethylphenyl}-methanol A solution of 4-[4-(butyl-ethyl-amino)-2,5-dimethyl-pyrrolo[2,3-d]pyrimidin-7-yl]-3,5-dimethyl-benzaldehyde (0.100 g, 0.264 mmol) in 1 ml MeOH was treated with sodium borohydride (0.030 g, 0.793 mmol) and stirred at room temperature for 20 minutes. The mixture was diluted with water and extracted with ethyl acetate. The organic layer was washed with brine, dried and concentrated to dryness to give a clear oil. The oil was purified through silica gel column chromatography to give the title compound (0.092 g, 92% yield) as a white solid, mp 93–95° C.

EXAMPLE 12

Butyl-ethyl-[7-(4-fluoromethyl-2,6-dimethyl-phenyl)-2,5-dimethyl-7H-pyrrolo[2,3-d]pyrimidin-4-yl]-amine A solution of {4-[4-(butyl-ethyl-amino)-2,5-dimethyl-pyrrolo[2,3-d]pyrimidin-7-yl]-3,5-dimethylphenyl}-methanol (0.071 g, 0.186 mmol) in 2 ml anhydrous methylene chloride was cooled to −78° C. and treated with dimethylaminosulfur trifluoride (0.063g, 0.390 mmol) and stirred at room temperature for 1 hour. The mixture was quenched with water and extracted with chloroform. The organic layer was washed with brine, dried, and concentrated to give an oil which was purified through silica gel using 2% methanol/chloroform as eluent to give the title compound as an off-white solid, mp 163–165° C.

EXAMPLE 13

Butyl-ethyl-{7[4-(1-methoxy-ethyl)-2,6-dimethyl-phenyl-2,5-dimethyl-7H-pyrrolo[2,3-d]pyrimidin-4-yl}-amine A solution of {4-[4-(butyl-ethyl-amino)-2,5-dimethyl-pyrrolo[2,3-d]pyrimidin-7-yl]-3,5-dimethylphenyl}-methanol (0.100 g, 0.263 mmol) in 1 ml of dry tetrahydrofuran was treated with sodium hydride (0.0116 g, 0.289 mmol, 60% in oil). After stirring for 10 minutes, an excess of methyl iodide was added. The mixture was quenched with water and extracted with ethyl acetate. The organic layer was washed with brine, dried and concentrated to give an oil. The oil was purified through silica gel column using 10% ethyl acetate in hexane as eluent to give 0.081 g (78%) of the title compound as a white glass form.

EXAMPLE 14

(4-aminomethyl-2,6-dimethyl-phenyl)-2,5-dimethyl-7H-pyrrolo[2,3-d]pyrimidin-4-yl]-butyl-ethyl-amine A solution of 4-[4-(butyl-ethyl-amino)-2,5-dimethyl-pyrrolo[2,3-d]pyrimidin-7-yl]3,5-dimethyl-benzaldehyde (0.200 g, 0.528 mmol) in 2 ml of methanol was treated with sodium cyanoborohydride (0.023 g, 0.37 mmol), ammonium acetate (0.407 g, 5.28 mmol) and sodium sulfate. After stirring for 1 hour, the mixture was concentrated to remove methanol and the residue was dissolved in water, saturated sodium bicarbonate and extracted with ethyl acetate. The organic layer was washed with brine, dried and concentrated to give an oil. The oil was purified through silica gel column using 10% methanol in chloroform as eluent to give the title compound as a clear oil. The corresponding di-HCl salt was prepared as a white solid, mp 158–160° C.

EXAMPLE 15

Butyl-ethyl-[7-(4-methoxy-ethyl-2,6-dimethyl-phenyl)-2,5-dimethyl-7H-pyrrolo[2,3-d]pyrimidin-4-yl]-amine The title compound was prepared starting from the 1-{4-[4-(butyl-ethyl-amino)-2,5-dimethyl-pyrrolo[2,3-d]pyrimidin-7-yl]-3,5-dimethyl-phenyl}-ethanol, sodium hydride and methyl iodide and employing the procedure of Example 13.

The $^1$H NMR data of the compounds prepared by the methods of Examples 8 to 15 are listed in the following Table.

TABLE I

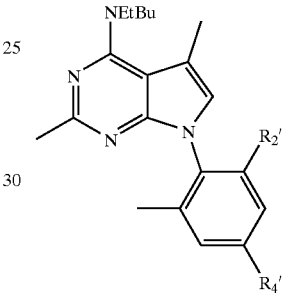

(C)

| Example | $R_2'$ | $R_4'$ | $^1$H NMR(CDCl$_3$) δ (ppm) |
|---|---|---|---|
| | Me | H | 0.93(t, 3H), 1.23(t, 3H), 1.25–1.40 (m, 2H), 1.55–1.60(m, 2H), 1.95(s, 6H), 2.42(s, 3H), 2.45(s, 3H), 3.58 (m, 2H), 3.64(q, 2H), 6.56(s, 1H), 7.05–7.20(M, 3H) |
| | Me | COOH | 0.95(t, 3H), 1.27(t, 3H), 1.3–1.45(m, 2H), 1.6–1.8(m, 2H), 1.96(s, 6H), 2.43(s, 3H), 2.56(s, 3H), 3.65(t, 2H), 3.72(q, 2H), 6.61(s, 1H), 7.52(s, 2H) |
| | Me | CHO | 0.92(t, 3H), 1.23(t, 3H), 1.25–1.40 (m, 2H), 1.55–1.70(m, 2H), 2.03(s, 6H), 2.42(s, 3H), 2.43(s, 3H), 3.58 (m, 2H), 3.64(q, 2H), 6.54(s, 1H), 7.65(s, 2H), 9.99(s, 1H) |
| | Me | CH2OH | 0.92(t, 3H), 1.22(t, 3H), 1.25–1.40 (m, 2H), 1.55–1.70(m, 2H), 1.94(s, 6H), 2.41(s, 3H), 2.45(s, 3H), 3.58(t, 2H), 3.65(q, 2H), 4.55(s, 2H), 6.54(s, 1H), 7.09(s, 2H) |
| | Me | CH(Me)(OH) | 0.91(t, 3H), 1.21(t, 3H), 1.2–1.4(m, 2H), 1.44(d, 3H), 1.5–1.7(m, 2H), 1.91(s, 6H), 2.39(s, 3H), 2.42(s, 3H), 3.57(t, 2H), 3.64(q, 2H), 4.75(q, 1H), 6.53(s, 1H), 7.11(s, 1H), 7.13(s, 1H) |
| | Me | COOMe | 0.92(t, 3H), 1.23(t, 3H), 1.25–1.30 (m, 2H), 1.5–1.7(m, 2H), 1.99(s, 6H), 2.41(s, 3H), 2.43(s, 3H), 3.58(t, 2H), 3.64(q, 2H), 3.91(s, 3H), 6.53(s, 1H), 7.81(s, 2H) |
| | Me | CH$_2$F | 0.90(t, 3H), 1.20(t, 3H), 1.24–1.40 (m, 2H), 1.5–1.7(m, 2H), 1.95(s, 6H), 2.38(s, 3H), 2.42(s, 3H), 3.54(t, 2H), 3.62(q, 2H), 4.30(d, 2H), 6.50 (s, 1H), 7.10(s, 2H) |
| | Me | CH$_2$NH$_2$ | 0.90(t, 3H), 1.20(t, 3H), 1.2–1.4(m, 2H), 1.5–1.7(m, 2H), 1.93(s, 6H), 2.40(s, 3H), 2.42(s, 3H), 3.54(t, 2H), |

TABLE I-continued (C)

| Example | R₂' | R₄' | ¹H NMR(CDCl₃) δ (ppm) |
|---|---|---|---|
|  | Me | CONHMe | 3.62(q, 2H), 3.82(s, 2H), 6.52(s, 1H), 7.10(s, 2H) 0.94(t, 3H), 1.2–1.4(m, 5H), 1.4–1.6 (m, 2H), 1.96(s, 6H), 2.43(s, 3H), 2.75(s, 1.5H), 2.82(s, 1.5H), 3.24(s, 1H), 3.5–3.8(m, 4H), 6.53(s, 1H), 7.22(s, 1H), 7.48(s, 1H) |
|  | Me | OH | 0.89(t, 3H), 1.20(t, 3H), 1.2–1.4(m, 2H), 1.5–1.7(m, 2H), 1.76(s, 6H), 2.379(s, 3H), 2.52(s, 3H), 3.58(t, 2H), 3.65(q, 2H), 6.26(s, 2H), 6.50(s, 1H) |
|  | Me | I | 0.92(t, 3H), 1.22(t, 3H), 1.2–1.35(m, 2H), 1.5–1.7(m, 2H), 1.89(s, 6H), 2.40(s, 3H), 2.44(s, 3H), 3.57(t, 2H), 3.64(q, 2H), 6.50(s, 1H), 7.48(s, 2H) |
|  | Me | Et | 0.93(t, 3H), 1.25(m, 6H), 1.2–1.4(m, 2H), 1.55–1.60(m, 2H), 1.92(s, 6H), 2.41(s, 3H), 2.46(s, 3H), 2.63(q, 2H), 3.57(t, 2H), 3.64(q, 2H), 6.55(s, 1H), 6.96(s, 2H) |
|  | Me | CH(Me)(OMe) | 0.88(t, 3H), 1.18(t, 3H), 1.2–1.4(m, 2H), 1.38(d, 3H), 1.5–1.7(m, 2H), 1.90(s, 6H), 2.36(s, 3H), 2.40(s, 3H), 3.24(s, 3H), 3.4–3.65(m, 4H), 4.20(q, 1H), 6.50(s, 1H), 7.00(s, 2H) |
|  | Me | CH₂OMe | 0.92(t, 3H), 1.22(t, 3H), 1.2–1.4(m, 2H), 1.5–1.65(m, 2H), 1.94(s, 6H), 2.41(s, 3H), 2.44(s, 3H), 3.42(s, 3H), 3.45–3.52(m, 4H), 4.42(s, 2H), 6.53 (s, 1H), 7.10(s, 2H) |
|  | Me | C(Me)₂(OH) | 0.92(t, 3H), 1.22(t, 3H), 1.25–1.40 (m, 2H), 1.5–1.7(m, 2H), 1.58(s, 6H), 1.95(s, 6H), 2.40(s, 3H), 2.45(s, 3H), 3.5–3.7(m, 4H), 6.54(s, 1H), 7.23(s, 2H) |

(D)

| NR₁R₂ | R₂' | R₄' | ¹H NMR(CDCl₃) δ (ppm) |
|---|---|---|---|
| NHCH(Et)₂ | Me | H | 0.98(t, 6H), 1.5–1.8(m, 4H), 1.97(s, 6H), 2.44(s, 3H), 2.46(s, 3H), 4.34(m, 1H), 4.81(d, 1H), 6.44(s, 1H), 7.1–7.2(m, 3H) |
| NHCH(Et)₂ | Me | CHO | 0.98(t, 6H), 1.5–1.8(m, 4H), 2.06(s, 6H), 2.43(s, 3H), 2.46(s, 3H), 4.31(m, 1H), 4.83(d, 1H), 6.43(s, 1H), 7.66(s, 1H), 9.99(s, 1H) |
| NHCH(Et)(CH₂OMe) | Me | H | 1.01(t, 3H), 1.4–1.6(m, 2H), 1.95(s, 6H), 2.42(s, 3H), 2.44(s, 3H), 3.40(s, 3H), 3.55(2 sets of ABq, 2H), 4.48(m, 1H), 5.26(d, 1H, NH), 6.43(s, 1H), 7.0–7.2(m, 3H) |

EXAMPLE 16

The following compounds of formula (C) were prepared by procedures analogous to those in Examples 8 to 15.

| R₂' | R₄' | ¹H NMR (CDCl₃) δ (ppm) |
|---|---|---|
| H | Me | 0.95(t,3H), 1.23(t,3H), 1.2–1.4(m,2H), 1.55–1.77(m,2H), 2.08(s,3H), 2.38(s,3H), 2.44(s,3H), 2.50(s,3H)3.59(t,2H), 3.66(q,2H), 6.71(ws,1H), 7.0–7.2(m,3H) |
| CHO | Me | 0.95(t,3H), 1.26(t,3H), 1.25–1.45(m,2H), 1.6–1.8(m,2H), 2.05(s,3H), 2.438(s,3H), 2.443(s,3H), 2.448(s,3H), 3.5–3.8(m,4H), 6.7(s,1H), 7.39(d,1H), 7.68((d,1H), 9.33(s,1H) |
| CH₂OH | Me | 0.96(t,3H), 1.27(t,3H), 1.25–1.45(m,2H), 1.6–1.75(m,2H), 1.95(s,3H), 2.41(s,3H), 2.43(s,3H), 2.44(s,3H), 3.5–3.8(m,4H), 4.15(m,2H), 6.6(s,1H), 7.11(s,1H), 7.26(s,1H) |

-continued

| $R_2'$ | $R_4'$ | $^1$H NMR (CDCl$_3$) δ (ppm) |
|---|---|---|
| CH$_2$F | Me | 0.96(t,3H), 1.28(t,3H), 1.25–1.45(m,2H), 1.6–1.8(m,2H), 1.95(s,3H), 2.41(s,3H), 2.43(s,3H), 2.46(s,3H), 3.5–3.8(m,4H), 5.01(2 sets of ABq,2H), 6.63(s,1H), 7.15(s,1H), 7.25(s,1H) |
| CH(Me)(OH) | Me | 0.96(t,3H), 1.27(t,3H), 1.25–1.409m,2H), 1.43(d,3H), 1.6–1.8(m,2H), 1.93(s,3H), 2.42(s,6H), 2.45(s,3H), 3.4–3.8(m,4H), 4.37(q,2H), 5.10(s,1H), 6.62(s,1H), 7.09(s,1H), 7.35(s,1H) |
| I | Me | 0.96(t,3H), 1.27(t,3H), 1.25–1.45(m,2H), 1.6–1.8(m,2H), 1.97(s,3H), 2.34(s,3H), 2.46(s,3H), 2.50(s,3H), 3.5–3.8(m,4H), 6.58(s,1H), 7.10(S,1H), 7.62(s,1H) |
| Cl | Me | 0.95(t,3H), 1.25(t,3H), 1.25–1.45(m,2H), 1.6–1.8(m,2H), 1.97(s,3H), 2.36(s,3H), 2.44(s,3H), 2.48(s,3H), 3.5–3.8(m,4H), 6.61(s,1H), 7.04(s,1H), 7.19(s,1H) |
| C(Me)$_2$(OH) | Me | 0.94(t,3H), 1.18(s,3H), 1.25(t,3H), 1.25–1.5(m,2H), 1.55(s,3H), 1.6–1.8(m,2H), 1.69(s,3H), 2.38(s,3H), 2.42(s,3H), 2.43(s,3H), 3.5–3.8(m,4H), 4.13(brs,1H), 6.57(s,1H), 7.04(s,1H), 7.39(s,1H) |
| CH$_2$NH$_2$ | Me | 0.96(t,3H), 1.26(t,3H), 1.3–1.5(m,2H), 1.6–1.8(M,2H), 1.85(s,3H), 2.28(S<3H), 2.38(s,6H), 3.28(q,2H), 3.5–3.8(m,4H), 6.58(s,1H), 6.93(s,1H), 6.99(s,1H) |
| CH$_2$OMe | Me | 0.96(t,3H), 1.26(t,3H), 1.25–1.45(m,2H), 1.6–1.8(m,2H), 1.92(s,3H), 2.38(s,3H), 2.44(s,3H), 2.46(s,3H), 3.25(s,3H), 3.61(t,2H), 3.68(q,2H), 4.04(ABq,2H), 6.62(s,1H), 7.06(s,1H), 7.22(s,1H) |
| Et | Me | 0.95(t,3H), 1.04(t,3H), 1.26(t,3H), 1.25–1.45(m,2H), 1.90(s,3H), 2.15–2.35(m,2H), 2.37(s,3H), 2.44(s,3H), 2.47(s,3H), 3.63(m,2H), 3.67(q,2H), 6.57(s,1H), 6.98(s,1H), 7.01(s,1H) |
| CH(Me)(OMe) | Me | 0.96(t,3H), 1.2–1.4(m,6H), 1.25–1.45(m,2H), 1.6–1.8(m,2H), 1.91(s,3H), 2.41(s,3H), 2.43(s,3H), 2.44(s,3H), 3.14(s,3H), 3.5–3.75(m,4H), 3.81(q,1H), 6.54(s,1H), 7.06(s,1H), 7.25(s,1H) |

EXAMPLE 17

4-sec-Butoxy-1-(2,5,6-tri methylphenyl-7-(2,4,6-trimethyl-phenyl)-7H-pyrrolo[2,3-d]pyrimidine Sodium hydride (0.114g, 4.77mmol, 60% in oil) was washed with hexane, then treated with 2-butanol (1.18g, 15.90 mmol). After 20 minutes, a mixture of 4-chloro-2,5,6-trimethyl-7-(2,4,6-trimethylphenyl)-7H-pyrrolo[2,3-d]pyrimidine (0.500 g, 1.59 mmol) in 5 ml of anhydrous tetrahydrofuran was added to the reaction mixture and stirred for 2 hours. The mixture was concentrated to dryness, dissolved in ethyl acetate and water. The organic layer was separated, washed with brine, dried, and concentrated to give a clear oil. The oil residue was purified through silica gel column chromatography using 20% ethyl acetate in hexane as eluent to give a clear oil which crystallized under high vacuo to give 0.450 g (80.5%) of an off-white solid. The solid was recrystallized from i-propanol to give gold crystals, mp 178–180° C.

EXAMPLE 18

The following compounds were prepared starting with the appropriate alcohol and 4-chloro-2,5,6-trimethyl-7-(2,4,6-trimethylphenyl)-7H-pyrrolo[2,3-d]pyrimidine or 4-chloro-2,5-dimethyl-7-(2,4,6-trimethylphenyl)-7H-pyrrolo[2,3-d]pyrimidine and employing the general procedure of Example 17.

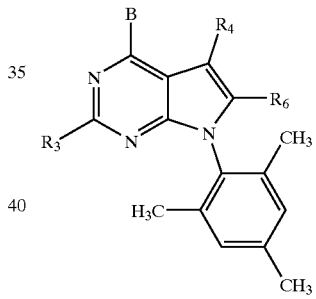

(A)

| B | $R_3$ | $R_4$ | $R_6$ | $^1$H NMR(CDCl$_3$) δ (ppm) |
|---|---|---|---|---|
| OCHMe$_2$ | Me | Me | Me | 1.41(d, 6H), 1.82(s, 6H), 1.91(s, 3H), 2.33(s, 3H), 2.36(s, 3H), 2.48(s, 3H), 5.55(m, 1H), 6.98(s, 2H) |
| OCHEt$_2$ | Me | Me | Me | 0.99(t, 6H), 1.74(m, 4H), 1.84(s, 6H), 1.92(s, 3H), 2.34(s, 3H), 2.37(s, 3H0), 2.48(s, 3H0), 5.34(m, 1H), 6.98(s, 2H) |
| OCHMe$_2$ | Me | Me | Me | 1.41(d, 6H), 1.82(s, 6H), 1.91(s, 3H), 2.33(s, 3H), 2.36(s, 3H), 2.48(s, 3H), 5.55(m, 1H), 6.98(s, 2H) |
| OCH(Me)(Et) | Me | Me | Me | 1.02(t, 3H), 1.28(d, 3H), 1.65–1.80 (m, 2H), 1.83(s, 6H), 1.92(s, 3H), 2.33(s, 3H), 2.37(s, 3H), 2.48(s, 3H), 5.38(m, 1H), 6.98(s, 2H) |
| OCH(Et)(n-Pr) | Me | Me | Me | 0.94(t, 3H), 0.97(t, 3H), 1.38–1.60 (m, 2H), 1.6–1.8(m, 4H), 1.82(s, 6H), 1.90(s, 3H), 2.32(s, 3H), 2.35(S, 3H), 2.46(s, 3H), 6.96(s, 2H) |
| OCH(Et)(n-Bu) | Me | Me | Me | 0.90(t, 3H), 0.99(t, 3H), 1.3–1.5(m, 4H), 1.6–1.8(m, 4H), 1.832(s, 3H), 1.837(s, 3H), 1.92(s, 3H), 2.34(s, 3H), 2.36(s, 3H), 2.48(s, 3H), 5.39 (m, 1H), 6.98(s, 2H) |
| OCH(Et)(n-pentyl) | Me | Me | Me | 0.88(t, 3H), 0.98(t, 3H), 1.4–1.6(m, 6H), 1.6–1.8(m, 4H), 1.82(s, 6H), |

-continued (A)

| B | R$_3$ | R$_4$ | R$_6$ | $^1$H NMR(CDCl$_3$) δ (ppm) |
|---|---|---|---|---|
| OCH(Et)(n-hexyl) | Me | Me | Me | 1.90(s, 3H), 2.32(s, 3H), 2.36(s, 3H), 2.47(s, 3H), 5.40(m, 1H), 6.96(s, 2H) 0.85(t, 3H), 0.97(t, 3H), 1.20–1.50 (m, 8H), 1.6–1.8(m, 4H), 1.82(s, 6H), 1.90(s, 3H), 2.32(s, 3H), 2.35(s, 3H), 2.469(s, 3H), 5.37(m, 1H), 6.96 (s, 2H) |
| OCH(n-Pr)$_3$ | Me | Me | Me | 0.94(t, 3H), 1.4–1.6(m, 4H), 1.6–1.8 (m, 4H), 1.83(s, 6H), 1.91(s, 3H), 2.33(s, 3H), 2.36(S, 3H), 2.48(s, 3H), 5.50(m, 1H), 6.97(s, 2H) |
| OCH(Et)(CH$_2$OMe) | Me | Me | Me | 1.03(s, 3H), 1.82(s, 3H), 1.83(s, 3H), 1.91(s, 3H), 2.33(s, 3H), 2.37(s, 3H), 2.47(s, 3H), 3.43(s, 3H), 3.68(m, 2H), 5.55(m, 1H), 6.97(s, 2H) |
| OCHEt$_2$ | Me | Me | H | 0.99(t, 6H), 1.63(m, 4H), 1.92(s, 6H), 2.32(s, 3H), 2.41(s, 3H), 2.50(s, 3H), 5.35(m, 1H), 6.52(s, 1H), 6.96 (s, 2H) |
| OCH(Et)(CH$_2$OMe) | Me | Me | H | 1.00(t, 3H), 1.6–1.8(m, 2H), 1.86(s, 3H), 1.87(s, 3H), 2.28(s, 3H), 2.40(s, 3H), 2.489(s, 3H0), 3.40(s, 3H), 3.62 (m, 2H), 5.51(m, 1H), 6.48(s, 1H), 6.92(s, 2H) |

EXAMPLE 19

2,5,6-Trimethyl-7-(2,4,6-trimethylphenyl)-7H-pyrrolo[2,3-d]pyrimidine-4-carbonitrile A mixture of 4-chloro-2,5,6-trimethyl-7-(2,4,6-trimethyl-phenyl)-7H-pyrrolo[2,3-d]-pyrimidine (10.000 g, 31.90 mmol) and potassium cyanide (20.75 g, 319 mmol) in 100 ml dimethylsulfoxide was heated at 130° C. oil bath over weekend. The mixture was diluted with water and extracted with ethyl acetate. The organic layer was washed with brine, dried over magnesium sulfate, and concentrated to give 9.61 g (99%) of brown soild. The solid was recrystallized from i-propanol to give 6.34 g (65%) of the title compound as light golden crystals, mp 188–190° C. $^1$H NMR (CDCl$_3$) δ 1.8(s, 6H), 2.07(s, 3H), 2.36(s, 3H), 2.50(s, 3H), 2.65(s, 3H), 7.00(s, 2H).

2-Methyl-1-[2,5,6-trimethyl-7-(2,4,6-trimethyl-phenyl)-7H-pyrrolo[2,3-d]pyrimidin-4-yl]-butan-1-one To a solution of sec-butyl magnesium chloride (1.5 ml, 3.0 mmol, 2 M in diethyl ether) in 24 ml of dry tetrahydrofuran was added 2,5,6-trimethyl-7-(2,4,6-trimethyl-phenyl)-7H-pyrrolo[2,3-d]pyrimidine-4-carbonitrile (0.814 g, 2.67 mmol) at room temperature and stirred for 5 hours. The mixture was quenched with 5 ml of 2N HCl, neutralized with saturated sodium bicarbonate, extracted with ethyl acetate. The organic layer was dried and concentrated to give a yellow solid. The solid was purified through silica gel column chromatography using chloroform as eluent to give 0.884 g (90%) of the title compound as yellow crystals, mp 133–135° C.

EXAMPLE 20

[2,5,6-Trimethyl-7-(2,4,6-trimethylphenyl)-7H-pyrrolo[2,3-d]pyrimidin-4-yl]-propan-1-one and 1-[2,5,6-Trimethyl-7-(2,4,6-trimethyl-phenyl)-7H-pyrrolo[2,3-d]pyrimidin-4-yl]-pentan-1-one were prepared starting from 2,5,6-trimethyl-7-(2,4,6-trimethyl-phenyl)-7H-pyrrolo[2,3-d]-pyrimidine-4-carbonitrile and n-BuLi and ethyl magnesium chloride and employing the general procedure of Example 19 B.

EXAMPLE 21

[2,5,6-Trimethyl-7-(2,4,6-trimethylphenyl)-7H-pyrrolo[2,3-d]pyrimidin-4-yl]- propan-1-ol A solution of 2,5,6-trimethyl-7-(2,4,6-trimethylphenyl)-7H-pyrrolo[2,3-d]pyrimidin-4-yl]-propan-1-one (0.300 g, 0.89 mmol) in 10 ml of methanol was treated with sodium borohydride (NaBH$_4$) (0.169 g, 4.47 mmol) at room temperature and stirred for 15 minutes. The mixture was quenched with water and extracted with ethyl acetate. The organic layer was dried, and concentrated to give 0.291 g (96%) of the title compound as light yellow crystals. The crystals were recrystallized from i-propanol to give light yellow crystals, mp 143–144° C.

EXAMPLE 22

The following compounds were prepared by reduction of the corresponding ketone derivative with NaBH$_4$ by the procedure described in the Example 21:

1-[2,5,6-Trimethyl-7-(2,4,6-trimethylphenyl)-7H-pyrrolo [2,3-d]pyrimidin-4-yl-pentan-ol; and 2-Methyl-1-[2,5,6-trimethyl-7-(2,4,6-trimethylphenyl)-7H-pyrrolo[2,3-d]pyrimidin-4-yl]-butan-ol.

EXAMPLE 23

The following compounds were prepared by reaction of the corresponding alcohol derivative with NaH, followed by reacting with alkyl iodide using the procedure analogous to that described in Example 13:

4-(1-Methoxy-propyl)-2,5,6-trimethyl-7-(2,4,6-trimethylphenyl)-7H-pyrrolo[2,3-d]pyrimidine;

4-(1-Ethoxy-propyl)-2,5,6-trimethyl-7-(2,4,6-trimethylphenyl)-7H-pyrrolo[2,3-d]pyrimidine; and 4-(1-Methoxy-2-methyl-butyl)-2,5,6-trimethyl-7-(2,4,6-trimethylphenyl)-7H-pyrrolo[2,3-d]pyrimidine.

EXAMPLE 24

[2,6-Trimethyl-7-(2,4,6-trimethyl-phenyl)-7H-pyrrolo[2,3-d]pyrimidin-4-yl]-pentan-3-ol A solution of 1-[2,5,6-trimethyl-7-(2,4,6-trimethylphenyl)-7H-pyrrolo[2,3-d]pyrimidin-4-yl]-propan-1-one (0.220 g, 0.656 mmol) in 10 ml of dry THF was treated with ethyl magnesium bromide (0.787 mmol, 0.39 ml, 2.0 m in THF) at 0° C. and stirred at room temperature for 1 hour. The mixture was quenched with diluted HCl, neutralized with aqueous NaOH and extracted with ethyl acetate. The organic layer was dried and concentrated to give

EXAMPLE 25

[2,5,6-Trimethyl-7-(2,4,6-trimethylphenyl)-7H-pyrrolo[2,3-d]pyrimidin-4-yl]-hexan-3-ol The title compound was prepared by reacting 1-[2,5,6-trimethyl-7-(2,4,6-trimethyl-phenyl)-7H-pyrrolo[2,3-d]pyrimidin-4-yl]-propan-1-one with n-propyl magnesium chloride using the procedure described in Example 24.

EXAMPLE 26

4-(1-Ethyl-1-fluoro-propyl)-2,5,6-trimethyl-7-(2,4,6-trimethylphenyl)-7H-pyrrolo[2,3-d]-pyrimidine The title compound was prepared by reacting 3-[2,5,6-trimethyl-7-(2,4,6-trimethylphenyl)-7H-pyrrolo[2,3-d]pyrimidin-4-yl]-pentan-3-ol with dimethylaminosulfur trifluoride using the procedure described in Example 12.

EXAMPLE 27

4-(1-Ethyl-propenyl)-2,5,6-trimethyl-7-(2,4,6-trimethylphenyl)-7H-pyrrolo[2,3-d]pyrimidine A mixture of 3-[2,5,6-trimethyl-7-(2,4,6-trimethylphenyl)-7H-pyrrolo[2,3-d]pyrimidin-4-yl]-pentan-3-ol (0.041 g, 0.122 mmol), concentrated sulfuric acid (0.055 g, 0.56 mmol) and acetic acid (0.136 g, 2.27 mmol) was heated to reflux for 1 hour, cooled, diluted with water, basified to pH10 with 2 N NaOH and extracted with ethyl acetate. The organic layer was washed with brine, dried and concentrated to dryness to give 43 mg of the title compound as a clear oil. The oil was purified through silica gel column chromatography to give 40 mg of the title compound as a white solid, mp 59–61° C.

EXAMPLE 28

Compounds listed in the following Table II in which B is CH(OAc)(CHMeEt) and a mixture of two isomers 4-(1-ethyl-butenyl)-2,5,6-trimethyl-7-(2,4,6-trimethylphenyl)-7H-pyrrolo[2,3-d]pyrimidine and 4-(1-n-propyl-propenyl)-2,5,6-trimethyl-7-(2,4,6-trimethyl -phenyl)-7H-pyrrolo[2,3-d]pyrimidine [see Table II in which B is C(═CHEt)(Et) and C(═CHMe)(n—Pr)] were prepared by a procedure analogous to that described in Example 27.

EXAMPLE 29

4-(1-Ethyl-butyl)-2,5,6-trimethyl-7-(2,4,6-trimethylphenyl)-7H-pyrrolo[2,3-d]pyrimidine A mixture of two isomers, 4-(1-ethyl-butenyl)-2,5,6-trimethyl-7-(2,4,6-trimethylphenyl)-7H-pyrrolo[2,3-d]pyrimidine and 4-(1-n-propyl-propenyl)-2,5,6-trimethyl-7-(2,4,6-trimethyl-phenyl)-7H-pyrrolo[2,3-d]pyrimidine (67 mg, 0.185 mmol) in ethyl acetate (18 ml) and 10% Pd/C (38 mg) was hydrogenated at 50 psi for 15 hours. The mixture was filtered through Celite, a trademark for a commercially available diatomaceous earth filtering material. The filtrate was washed with brine, dried and concentrated to give 119 mg of oil. The oil was purified through silica gel column chromatography using 7% ethyl acetate in hexane as eluent to give 31 mg (46%) of the title compound as off-white crystals, mp 100–102° C.

EXAMPLE 30

[-2,5,6-Trimethyl-7-(2,4,6-trimethylphenyl)-7H-pyrrolo[2,3-d]pyrimidin-4-yl]- propan-1-one oxime A mixture of 1-[-2,5,6-trimethyl-7-(2,4,6-trimethylphenyl)-7H-pyrrolo[2,3-d]pyrimidin-4-yl]-propan-1-one (0.598 g, 1.783 mmol), hydroxylamino hydrochloride (0.370 g, 5.35 mmol), sodium acetate (0.439 g, 5.35 mmol) in MeOH (30 ml) was stirred at room temperature for 24 hours. The mixture was concentrated to dryness. The residue was diluted with water and extracted with ethyl acetate. The organic layer was dried and concentrated to give 0.657 g of a white glassy foam. The glassy foam was purified through silica gel column chromatography to separated both E (white crystals, mp 162–164° C., confirmed by X-ray structural analysis) and Z (white crystals, mp 84–87° C.) isomers and a mixture of E and Z isomers (mp –150–190° C.).

EXAMPLE 31

1-[2,5,6-Trimethyl-7-(2,4,6-trimethylphenyl)-7H-pyrrolo[2,3-d]pyrimidin-4-yl]-propylamine Hydrogenation of 1-[-2,5,6-Trimethyl-7-(2,4,6-trimethyl phenyl )-7H-pyrrolo[2,3-d]-pyrim-idin-4-yl]-propan-1-one oxime with 10% Pd/C in MeOH using the general procedure described in Example 29 resulted in the title compound.

The $^1$H NMR data of the compounds which are described in the Examples 19 to 31 are listed in the following Table.

TABLE II (E)

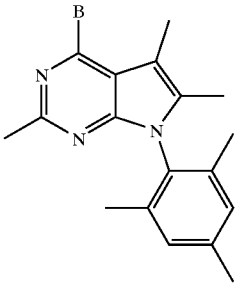

| B | $^1$H NMR(CDCl$_3$) δ (ppm) |
|---|---|
| CO-(n-Bu) | 1.00(t, 3H), 1.4–1.6(m, 2H), 1.7–1.9(m, 2H), 1.83(s, 8H), 2.06(s, 3H), 2.34(s, 3H), 2.35(s, 3H), 2.38 (s, 3H), 3.27(t, 2H), 7.03(s, 2H) |
| COEt | 1.26(t, 3H), 1.81(s, 6H), 2.04(s, 3H), 2.32(s, 3H), 2.36(s, 3H), 2.68 (s, 3H), 3.27(q, 2H), 7.00(s, 2H) |
| CO—CH(Me)(Et) | 0.99(t, 3H), 1.24(d, 3H), 1.45–1.65 (m, 1H), 1.7–1.9(m, 1H), 1.83(s, 6H), 2.05(s, 3H), 2.30(s, 3H), 2.37 (s, 3H), 2.68(s, 3H), 3.91(m, 1H0), 7.03(s, 2H) |
| CH(OH)(n-Bu) | 0.95(t, 3H), 1.2–1.8(m, 6H), 1.77 (s, 3H), 1.87(s, 3H), 2.00(s, 3H), 2.37(s, 3H), 2.39(s, 3H), 2.63(s, 3H), 5.20(dd, 1H), 7.02(s, 2H) |
| CH(OH)(Et) | 1.12(t, 3H), 1.6–2.0(m, 2H), 1.77 (s, 3H), 1.87(s, 3H), 2.00(s, 3H), 2.37(s, 3H), 2.39(s, 3H), 2.63(s, 3H), 4.97(d, 1H), 5.15(m, 1H), 7.02(s, 2H) |

TABLE II-continued (E)

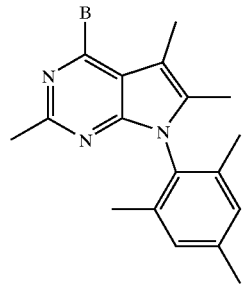

| B | $^1$H NMR(CDCl$_3$) δ (ppm) |
|---|---|
| CH(OMe)(Et) | 1.02(t, 3H), 1.82(s, 3H), 1.83(s, 3H), 2.01(s, 3H), 1.8–2.1(m, 2H), 2.36(s, 3H), 2.45(s, 3H), 2.669(s, 3H), 3.359(s, 3H0), 4.68(t, 1H), 7.01(s, 2H) |
| CH(OEt)(Et) | 1.02(t, 3H), 1.22(t, 3H), 1.82(s, 3H), 1.83(s, 3H), 1.7–2.1(m, 2H), 2.36(s, 3H), 2.46(s, 3H), 2.65(s, 3H), 3.49(m, 2H), 4.75(t, 1H), 7.01(s, 2H) |
| CH(OMe)(CHMeEt) | 0.68(d, 1.8H), 0.83(t, 1.2H), 0.95 (t, 1.8H), 1.10(d, 1.2H), 1.1–1.5 (m, 2H), 1.9–2.2(m, 1H), 1.8(3 sets of s, 6H), 2.0(s, 3H), 2.359(s, 3H0), 2.53(s, 3H0), 2.65(s, 3H), 3.25(s, 1.8H), 3.30(s, 1.2H), 4.42 (d, 0.6H), 4.5(d, 0.4H), 7.0(s, 2H) |
| CH(OAc)(CHMeEt) | 0.7(d, 1.5H), 0.85(t, 1.5H), 0.94(t, 1.5H), 1.1(d, 1.5H), 1.1–1.5(m, 2H), 1.81(s, 1.5H), 1.83(s, 3H), 1.869(s, 1.5H), 2.0(s, 3H), 2.22(s, 1.5H), 2.24(s, 1.5H), 2.2–2.4(m, 0.5H), 2.32(s, 3H), 2.49(s, 1.5H), 2.51(s, 1.5H), 2.60(s, 3H), 3.0–3.2 (m, 0.5H), 6.12(m, 1H), 7.0(s, 2H) |
| CFEt$_2$ | 0.90(t, 6H), 1.83(s, 6H), 2.03(s, 3H), 2.0–2.4(m, 4H), 2.38(s, 6H), 2.59(s, 3H), 7.02(s, 2H) |
| CEt$_2$(OH) | 0.71(t, 6H), 1.79(s, 6H), 2.02(s, 3H), 2.0–2.4(m, 4H), 2.36(s, 3H), 2.47(s, 3H), 2.61(s, 3H), 7.01(s, 2H) |
| C(Et)(n-Pr)(OH) | 0.71(t, 3H), 0.84(t, 3H), 1.4–1.6 (m, 2H), 1.80(s, 3H), 1.81(s, 3H), 2.04(s, 3H), 1.9–2.2(m, 4H), 2.38 (s, 3H), 2.49(s, 3H), 2.63(s, 3H), 6.83(s, 1H), 7.03(s, 2H) |
| CH(Et)(NH-n-Pr) | 0.87(t, 3H), 0.90(t, 3H), 1.5–1.7 (m, 2H), 1.80(s, 3H), 1.83(s, 3H), 2.00(s, 3H), 1.9–2.2(m, 2H), 2.36 (s, 3H), 2.41(s, 3H), 2.42(s, 3H), 2.3–2.5(m, 1H), 2.7–2.9(m, 1H), 4.48(m, 1H), 7.019(s, 2H), 7.15(s, 1H), |
| C(=NOH)(Et) | 1.0–1.2(m,3H), 1.79(s, 1.5H), 1.80 (s, 1.5H), 1.99(s, 1.5H), 2.00(s, 1.5H), 2.22(s, 3H0), 2.35(s, 3H), 2.65(s, 1.5H), 2.68(s, 1.5H), 2.7(q, 1H), 2.99(q, 1H), 6.93(s, 2H), 9.05 (brs, 1H) |
| CH(Et)(NH2) | 1.04(t, 3H), 1.79(s, 3H), 1.85(s, 3H), 1.7–2.0(m, 2H), 1.99(s, 3H), 2.36(s, 3H), 2.42(s, 3H), 2.62(s, 3H), 4.52(m, 1H), 7.01(s, 2H) |
| C(=CHMe)(Et) | 1.00(t, 2.1H), 1.1(t, 0.9H), 1.47(d, 0.9H), 1.82(s, 6H), 1.9(d, 2.1H), 2.02(s, 3H), 2.25(s, 3H), 2.4–2.8 (m, 5H), 5.6–5.8(m, 1H), 7.0(s, 2H) |
| C(=CHEt)(Et) + C(=CHMe)(n-Pr) | (m, 5.4H), 1.82(s, 6H), 1.869(d, 1.8H), 2.0(s, 3H), 2.20(s, 1.2H), 2.21(s, 1.8H), 2.359(s, 3H), 2.60(s, 1.8H), 2.61(s, 1.2H), 2.3–2.8(m, 2.8H), 5.4–5.8(m, 1H), 6.959(s, 2H) |
| CH(n-Bu)(Et) | 0.83(t, 3H), 0.88(t, 3H), 1.1–1.49 (m, 2H), 1.6–2.2(m, 4H), 1.82(s, 3H), 1.83(s, 3H), 1.98(s, 3H), 2.35 (s, 3H), 2.43(s, 3H), 2.61(s, 3H), 3.33(m, 1H), 7.00(s, 2H) |

The following Preparations illustrate the synthesis of intermediates.

Preparation 1

The following compounds were prepared starting from the appropriate aniline and employing the general procedure of Example 1A.

(F)

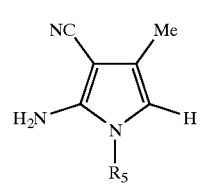

| R$_5$ | $^1$H-NMR(CDCl$_3$) δ (ppm) |
|---|---|
| 3,5-ditrifluoromethylphenyl | 2.2(s, 3H), 4.0(s, 2H), 6.15(s, 1H), 7.9(s, 2H) |
| 2,5-dimethylphenyl | 2.04(s, 3H), 2.12(s, 3H), 2.35(s, 3H), 3.85 (s, 2H), 5.90(s, 1H), 7.0(s, 1H), 7.10–7.25(m, 2H) |
| 2-methyl-4-iodophenyl | 2.05(s, 3H), 2.10(s, 3H), 3.80(s, 2H), 5.85 (s, 1H), 6.92(d, 1H), 7.60(dd, 1H), 7.70(d, 1H) |
| 3-methyl-4-chlorophenyl | 2.10(s, 3H), 2.40(s, 3H), 4.03(s, 2H), 6.03 (s, 1H), 7.10(dd, 1H), 7.21(d, 1H), 7.45(d, 1H) |
| 4-bromo-2,6-dimethylphenyl | 2.01(s, 6H), 2.10(s, 3H), 3.70(brs, 2H), 5.72(s, 1H), 7.30(s, 2H) |
| 2-bromo-4,6-dimethylphenyl | 2.06(s, 3H), 2.13(s, 3H), 2.35(s, 3H), 3.83 (brs, 2H), 5.81(s, 1H), 7.08(s, 1H), 7.35(s, 3H) |

Preparation 2

The following compounds were prepared starting from 3-hydroxy-2-butanone or 4-hydroxy-3-hexanone and the appropriate aniline and employing the general procedure of Example 2A.

(IV)

[Structure IV: pyrrole with NC, R4, R6, H2N, R5 substituents]

| R4 and R6 | R5 | ¹H-NMR(CDCl₃) δ (ppm) |
|---|---|---|
| Me | 2,4-dimethylphenyl | 1.70(s, 3H), 1.95(s, 3H), 2.05(s, 3H), 2.38(s, 3H), 3.7(s, 2H), 6.95–7.20(m, 3H) |
| Me | 2,6-dimethylphenyl | 1.67(s, 3H), 1.98(s, 6H), 2.05(s, 3H), 2.90(brs, 2H), 7.05–7.21(m, 3H) |
| Et | 2,4,6-trimethylphenyl | No purification; the material was used directly for the next reaction step |

Preparation 3

The following compounds were prepared starting from the corresponding compounds of preparations 1 and 2 and employing the general procedures of Examples 1B and 1C.

(G)

[Structure G: pyrrolopyrimidine with OH, R4, R6, H3C, R5 substituents]

¹H-NMR(solvent) δ (ppm)

R₄ = Me, R₆ = H

| R₅ | |
|---|---|
| R₅ = 3,5-ditrifluoromethylphenyl | (DMSO-d6) 2.32(s, 3H), 7.50(s, 1H), 8.05(s, 1H), 8.55(s, 1H), 12.10(s, 1H) |
| R₅ = 2,5-dimethylphenyl | (CDCl₃) 2.04(s, 3H), 2.35(s, 3H), 2.467 (s, 3H), 2.470(s, 3H), 6.57(s, 1H), 7.0–7.3(m, 3H), 12.08(s, 3H) |
| R₅ = 3-methyl-4-chlorophenyl | (DMSO-d₆) 2.29(s, 3H), 2.31(s, 3H), 2.38(s, 3H), 7.12(s, 1H), 7.55(m, 2H), 7.67(d, 1H), 11.90(s, 1H) |
| R₅ = 4-bromo-2,6-dimethylphenyl | (CDCl₃) 1.94(s, 6H), 2.40(s, 3H), 2.45 (s, 3H), 6.39(s, 1H), 7.29(s, 2H) |
| R₅ = 2-bromo-4,6-dimethylphenyl | (DMSO-d₆) 1.91(s, 3H), 2.20(s, 3H), 2.32(s, 3H), 2.34(s, 3H), 6.68(s, 1H), 7.21(s, 1H), 7.44(s, 1H), 11.80(s, 1H) |

R₄ & R₅ = Me

| R₅ = 2,4,6-trimethylphenyl | (CDCl₃) 1.85(s, 6H), 1.87(s, 3H), 2.34 (s, 3H), 2.41(s, 3H), 2.44(s, 3H), 7.00 (s, 2H), 12.2(s, 1H) |
| R₅ = 2,4-dimethylphenyl | (CDCl₃) 1.90(s, 3H), 1.93(s, 3H), 2.38 (s, 3H), 2.42(s, 6H), 7.0–7.2(m, 3H), 12.25(s, 1H) |
| R₅ = 2,6-dimethylphenyl | (CDCl₃) 1.80–1.90(m, 9H), 2.39(s, 3H), 2.49(s, 3H), 7.04–7.20(m, 3H), 12.2(s, 1H) |

Preparation 4

The following compounds were prepared starting from the corresponding compounds of Preparation 3 and employing the general procedure in Example 1D.

(V)

[Structure V: chloropyrrolopyrimidine with Cl, R4, R6, H3C, R5 substituents]

¹H-NMR(CDCl₃) δ (ppm)

R₄ = Me, R₆ = H

| R₅ = 3,5-ditrifluoromethylphenyl | 2.53(s, 3H), 2.74(s, 3H), 7.27(s, 1H), 7.82(s, 1H), 8.29(s, 2H) |
| R₅ = 2,5-dimethylphenyl | 2.01(s, 3H), 2.35(s, 3H), 2.50(s, 3H), 2.66(s, 3H), 6.91(s, 1H), 7.05(s, 1H), 7.10–7.30(m 2H) |
| R₅ = 3-methyl-4-chlorophenyl | 2.46(s, 3H), 2.51(s, 3H), 2.74(s, 3H), 7.15(s, 1H), 7.47(s, 2H), 7.55(s, 1H) |
| R₅ = 4-bromo-2,6-dimethylphenyl | 1.89(s, 6H), 2.49(s, 3H), 2.62(s, 3H), 6.75(s, 1H), 7.32(s, 2H) |
| R₅ = 2-bromo-4,6-dimethylphenyl | 1.96(s, 3H), 2.37(s, 3H), 2.52(s, 3H), 2.65(s, 3H), 6.82(s, 1H), 7.11(s, 1H), 7.38(s, 1H) |

R₆ = Me

| R₅ = 2,4,6-trimethylphenyl | 1.81(s, 6H), 1.99(s, 3H), 2.35(s, 3H), 2.46(s, 3H), 2.59(s, 3H), 7.01(s, 2H) |
| R₅ = 2,4-dimethylphenyl | 1.84(s, 3H), 2.03(s, 3H), 2.39(s, 3H), 2.44(s, 3H), 2.59(s, 3H), 6.90–7.15(m, 3H) |
| R₅ = 2,6-dimethylphenyl | 1.83(s, 6H), 1.98(s, 3H), 2.45(s, 3H), 2.58(s, 3H), 7.10–7.30(m, 3H) |

R₄ & R₆ = Et

| R₅ = 2,4,6-trimethylphenyl | 0.96(t, 3H), 1.31(t, 3H), 1.85(s, 6H), 2.38(s, 6H), 2.46(q, 2H), 2.62(s, 3H), 2.92(q, 2H), 7.02(s, 2H) |

What is claimed is:

1. A compound of the formula

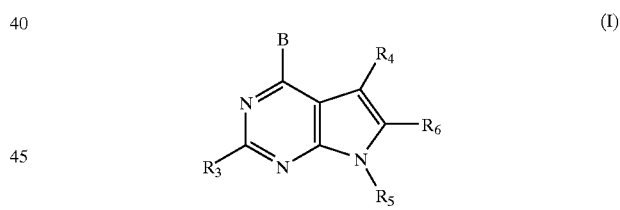

(I)

and the acid addition salts thereof, wherein B is $NR_1R_2$, $CR_1R_2R_{11}$, $C(=CR_2R_{12})R_1$, $NH-CR_1R_2R_{11}$, $O-CR_1R_2R_{11}$, $SCR_1R_2R_{11}$, $NHNR_1R_2$, $CR_2R_{11}NHR_1$, $CR_2R_{11}OR_1$, $CR_2R_{11}SR_1$, or $C(=O)R_2$; wherein:

$R_1$ is hydrogen, or monovalent $C_1-C_6$ aliphatic hydrocarbon which may be substituted by one or two substituents $R_7$ wherein $R_7$ is independently selected from the group consisting of hydroxy, fluoro, chloro, bromo, iodo, $C_1-C_6$ alkoxy, $O-C(=O)-(C_1-C_6$ alkyl), $O-C(=O)-NH(C_1-C_4$ alkyl), $O-C(=O)-N(C_1-C_4$ alkyl)($C_1-C_2$ alkyl), amino, $NH(C_1-C_4$ alkyl), $N(C_1-C_2$ alkyl)($C_1-C_4$ alkyl), $S(C_1-C_6$ alkyl), $N(C_1-C_4$ alkyl)—$C(=O)-(C_1-C_4$ alkyl), $NH-C(=O)-(C_1-C_4$ alkyl), $C(=O)OH$, $C(=O)-O-(C_1-C_4$ alkyl), $C(=O)-NH(C_1-C_4$ alkyl), $C(=O)-N-(C_1-C_4$ alkyl)($C_1-C_2$ alkyl), $SH$, $CN$, $NO_2$, $SO(C_1-C_4$ alkyl), $SO_2(C_1-C_4$ alkyl), $SO_2NH(C_1-C_4$ alkyl), and $SO_2N(C_1-C_4$ alkyl)($C_1-C_2$ alkyl); and wherein said monovalent $C_1-C_6$ aliphatic hydrocarbon may contain one or two double or triple bonds;

$R_2$ is monovalent $C_1$–$C_{12}$ aliphatic hydrocarbon; aryl; divalent $C_1$–$C_{10}$ aliphatic hydrocarbon)aryl wherein said aryl is phenyl, naphthyl, thienyl, benzothienyl, pyridyl, quinolyl, pyrazinyl, pyrimidyl, imidazolyl, furanyl, benzofuranyl, bonzothiazolyl, isothiazolyl, benzisothiazolyl, thiazolyl, isoxazolyl, benzisoxazolyl, benzimidazolyl, triazolyl, pyrazolyl, pyrrolyl, indolyl, pyrrolopyridyl, oxazolyl, or benzoxazolyl; 3- to 8-membered cycloalkyl; or ($C_1$-$C_6$ alkylene) cycloalkyl, wherein one or two methylene groups of said cycloalkyl may be independently replaced by one or two O, S or N—Z radicals wherein Z is hydrogen, $C_1$-$C_4$ alkyl, benzyl or $C_1$-$C_4$ alkanoyl, wherein $R_2$ may be substituted independently by from one to three of chloro, fluoro, or $C_1$-$C_4$ alkyl; or one of hydroxy, bromo, iodo, $C_1$-$C_6$ alkoxy, O—C(=O)—($C_1$-$C_6$ alkyl), O—C(=O)—N($C_1$-$C_4$ alkyl)($C_1$-$C_2$ alkyl), S($C_1$-$C_6$ alkyl), $NH_2$, NH($C_1$-$C_2$ alkyl), N($C_1$-$C_2$ alkyl)($C_1$-$C_4$ alkyl), N($C_1$-$C_4$ alkyl)—C(=O)—($C_1$-$C_4$ alkyl), NH—C(=O)—($C_1$-$C_4$ alkyl), C(=O)OH, C(=O)—O—($C_1$-$C_4$ alkyl), C(=O)—NH—($C_1$-$C_4$ alkyl), C(=O)—N—($C_1$-$C_4$ alkyl)($C_1$-$C_2$ alkyl), SH, CN, $NO_2$, SO($C_1$-$C_4$ alkyl), $SO_2$($C_1$-$C_4$ alkyl), $SO_2$NH ($C_1$-$C_4$ alkyl), or $SO_2$N($C_1$-$C_4$ alkyl)($C_1$-$C_2$ alkyl), and wherein said monovalent $C_1$–$C_{12}$ aliphatic hydrocarbon or divalent $C_1$-$C_{10}$ aliphatic hydrocarbon may contain one to three double or triple bonds; or $NR_1R_2$ taken together or $CR_1R_2R_{11}$ taken together may form saturated 3- to 8-membered carbocyclic rings, wherein said rings having from 5 to 8 members may contain one or two double bonds or one or two O, S or N—Z radicals wherein Z is hydrogen, $C_1$-$C_4$ alkyl, benzyl or $C_1$-$C_4$ alkanoyl;

$R_3$ is hydrogen, monovalent $C_1$–$C_6$ aliphatic hydrocarbon, fluoro, chloro, bromo, iodo, hydroxy, amino, O(monovalent $C_1$-$C_6$ aliphatic hydrocarbon), NH(monovalent $C_1$-$C_6$ aliphatic hydrocarbon), N(monovalent $C_1$-$C_4$ aliphatic hydrocarbon)($C_1$-$C_2$ alkyl), SH, S(monovalent $C_1$-$C_4$ aliphatic hydrocarbon), SO(monovalent $C_1$-$C_4$ aliphatic hydrocarbon), or $SO_2$(monovalent $C_1$-$C_4$ aliphatic hydrocarbon), wherein said monovalent $C_1$-$C_4$ aliphatic hydrocarbon and said monovalent $C_1$-$C_6$ aliphatic hydrocarbon may contain one or two double or triple bonds and may be substituted by from one to three substituents $R_8$ wherein R8 is independently selected from the group consisting of hydroxy, amino, $C_1$-$C_3$ alkoxy, dimethylamino, diethylamino, methylamino, ethylamino, NH—C(=O)—$CH_3$, fluoro, chloro and] $C_1$-$C_3$ alkylthio;

$R_4$ is hydrogen, $C_1$-$C_6$ alkyl, fluoro, chloro, bromo, iodo, $C_1$-$C_6$ alkoxy, amino, NH($C_1$-$C_6$ alkyl), N($C_1$-$C_6$ alkyl) ($C_1$-$C_2$ alkyl), $SO_n$($C_1$-$C_6$ alkyl), wherein n is 0, 1 or 2, cyano, hydroxy, carboxy, or amido, wherein said $C_1$-$C_6$ alkyls may be substituted by one hydroxy, trifluoromethyl, amino, carboxy, amido, NH—C (=O)—($C_1$-$C_4$ alkyl), NH($C_1$-$C_4$ alkyl), N($C_1$-$C_4$ alkyl)($C_1$-$C_2$ alkyl), C(=O)—O—($C_1$-$C_4$ alkyl), $C_1$-$C_3$ alkoxy, $C_1$-$C_3$ alkylthio, fluoro, bromo, chloro, iodo, cyano or nitro;

$R_5$ is phenyl, naphthyl, thienyl, benzothienyl, pyridyl, quinolyl, pyrazinyl, pyrimidyl, imidolyl, furanyl, benzofuranyl, benzothiazolyl, isothiazolyl, benzisothiazolyl, thiazolyl, isoxazolyl, benzisoxazolyl, benzimidazolyl, triazolyl, pyrazolyl, pyrrolyl, indolyl, azaindolyl, benzoxazolyl, oxazolyl, pyrrolidinyl, thiazolidinyl, morpholinyl, piperidinyl, piperaznyl, tetrazoiyl, or 3- to 8-membered cycloalkyl or 9 to 12-membered bicycloalkyl, optionally containing one to three O, S or N—Z radicals wherein Z is hydrogen, $C_1$-$C_4$ alkyl, $C_1$-$C_4$ alkanoyl, phenyl or phenylmethyl; wherein each one of the above groups may be substituted independently by from one to four of fluoro, chloro, monovalent $C_1$-$C_6$ aliphatic hydrocarbon, $C_1$-$C_6$ alkoxy or trifluoromethyl, or one of bromo, iodo, cyano, nitro, amino, NH(monovalent $C_1$-$C_6$ aliphatic hydrocarbon), N(monovalent $C_1$-$C_6$ aliphatic hydrocarbon)($C_1$–$C_2$ alkyl), COO(monovalent $C_1$-$C_4$ aliphatic hydrocarbon), CO(monovalent $C_1$-$C_4$ aliphatic hydrocarbon), $SO_2$NH-(monovalent $C_1$-$C_4$ aliphatic hydrocarbon), $SO_2$N (monovalent $C_1$-$C_4$ aliphatic hydrocarbon)($C_1$–$C_2$ alkyl), $SO_2NH_2$, $NHSO_2$ (monovalent $C_1$-$C_4$ aliphatic hydrocarbon), S(monovalent $C_1$-$C_6$ aliphatic hydrocarbon), or $SO_2$ (monovalent $C_1$-$C_6$ aliphatic hydrocarbon), wherein said monovalent $C_1$-$C_4$ aliphatic hydrocarbon and said monovalent $C_1$-$C_6$ aliphatic hydrocarbon may be substituted by one or two of fluoro, chloro, hydroxy, amino, methylamino, dimethylamino or acetyl; and wherein said monovalent $C_1$-$C_4$ aliphatic hydrocarbon and said monovalent $C_1$-$C_6$ aliphatic hydrocarbon may contain one double or triple bond;

$R_6$ is hydrogen, $C_1$-$C_6$ alkyl, fluoro, chloro, bromo, iodo, $C_1$-$C_6$ alkoxy, formyl, amino, NH($C_1$-$C_6$ alkyl), N($C_1$-$C_6$ alkyl)($C_1$-$C_2$ alkyl), $SO_n$($C_1$-$C_6$ alkyl) wherein n is 0, 1 or 2, cyano, carboxy, or amido, wherein said $C_1$-$C_6$ alkyls may be substituted by one hydroxy, trifluoromethyl, amino, carboxy, amido, NH—C (=O)—($C_1$-$C_4$ alkyl), NH($C_1$-$C_4$ alkyl), N($C_1$-$C_4$ alkyl)($C_1$-$C_2$ alkyl), C(=O)—O—($C_1$-$C_4$ alkyl), $C_1$-$C_3$ alkoxy, $C_1$-$C_3$ alkylthio, fluoro, bromo, chloro, iodo, cyano or nitro;

$R_{11}$, is hydrogen, hydroxy, fluoro, chloro, C(=O)—O—($C_1$-$C_2$alkyl), cyano, or C(=O)($C_1$-$C_2$ alkyl); and $R_{12}$ is hydrogen or $C_1$-$C_4$ alkyl;

WITH THE PROVISO THAT:
(1) when $R_5$ is pbromophenyl, and $R_3$, $R_4$ and $R_6$ are methyl, then B is not methylamino or hydroxyethylamino;
(2) when $R_5$ is unsubstituted phenyl or unsubstituted cycloelkyl, then $R_3$ and $R_4$ are hydrogen, and $R_6$ is hydrogen or methyl, then B is not NH substituted by furanylmethyl, benzyl, or thienylmetyl;
(3) when B represents $CR_1R_2R_{11}$ and both of $R_1$ and $R_{11}$ represent hydrogen, then $R_2$ does not represent straight chain $C_1$–$C_{12}$ alkyl;
(4) when $R_5$ is p-brorophenyl, $R_4$ and $R_6$ are methyl and $R_3$ is hydrogen, then B does not represent thioethyl or methylamino; and
(5) when $R_6$ is substituted cyclobutane, then $R_4$ is ($C_1$–$C_6$) alkyl;

that is effective in treating or preventing said disease.

2. A compound according to claim 1 wherein B is $NR_1R_2$, $NCHR_1R_2$ or $OCHR_1R_2$ wherein $R_1$ is monovalent $C_1$–$C_6$ aliphatic hydrocarbon which may be substituted by one of hydroxy, fluoro or $C_1$–$C_2$ alkoxy, and may contain one double bond or triple bond, and $R_2$ is benzyl or $C_1$–$C_6$ alkyl which may contain one double or triple bond, wherein said $C_1$–$C_6$ alkyl or the phenyl in said benzyl may be substituted by fluoro, $C_1$–$C_6$ alkyl, or $C_1$–$C_6$ alkoxy.

3. A compound according to claim 1 wherein B is $CR_1R_2R_{11}$ wherein $R_1$ is $C_1$–$C_6$ alkyl monovalent $C_1$–$C_6$ aliphatic hydrocarbon which may be substituted by one $C_1$–$C_6$ alkoxy or hydroxy, $R_2$ is benzyl or $C_1$–$C_6$ alkyl wherein said $C_1$–$C_6$ alkyl or the phenyl in said benzyl may be substituted by one $C_1$–$C_6$ alkyl, $C_1$–$C_6$ alkoxy, fluoron chloro or bromo, and $R_{11}$ is hydrogen or fluoro.

4. A compound according to claim 1 wherein B is as defined in claim 1 and $R_2$ is $C_1$–$C_6$ alkyl which may be substituted by fluoro, $C_1$–$C_6$ alky), or $C_1$–$C_6$ alkoxy and may contain one double or triple bond.

5. A compound according to claim 1 wherein B is as defined in claim 1 and $R_2$ is benzyl or methylthienyl, the phenyl or thienyl of which may be substituted by fluoro, chloro, $C_1$–$C_4$ alkyl or $C_1$–$C_4$ alkoxy.

6. A compound according to claim 1 wherein $R_3$ is methyl, ethyl, fluoro, chloro or methoxy.

7. A compound according to claim 1 wherein $R_4$ and $R_8$ are hydrogen, methyl, or ethyl.

8. A compound according to claim 1 wherein $R_5$ is phenyl substituted by two or three substituents.

9. A compound of the formula and prodrug and metabolite derivatives thereof affording pharmaceutically active species, and pharmaceutically acceptable acid addition salts thereof, wherein:

$R_1$ and $R_2$ are independently selected from the group consisting of methyl, ethyl, n-propyl, i-propyl, n-butyl, i-butyl, s-butayl, prop-2-en-1-yl, and 2-methylprop-2-en-1-yl, each methyl, ethyl and n-propyl optionally and independently substituted by a member selected from the group consisting of hydroxy, methoxy, cyclopropyl, tolyl, and dimethylamino;

$R_3$ and $R_4$ are independently hydrogen or methyl;

$R_6$ is hydrogen, methyl or ethyl;

$R_{13}$ is a member selected from the group consisting of hydrogen, bromo, chloro, iodo, formyl, methyl, ethyl or propyl, wherein each methyl, ethyl or propyl is optionally and independently substituted by fluoro, hydroxy, methoxy or amino;

$R_{14}$ is a member selected from the group consisting of hydrogen, bromo, chloro, methyl, and ethyl, wherein each methyl or ethyl is optionally and independently substituted by fluoro, hydroxy, methoxy or amino; and $R_{16}$ is bromo or methyl.

10. A compound of the formula

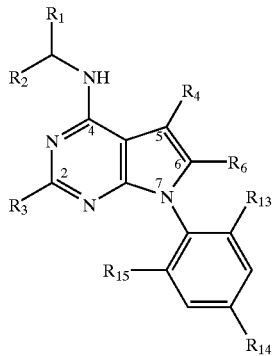

and prodrug and metabolite derivatives thereof affording pharmaceutically active species, and pharmaceutically acceptable acid addition salts thereof, wherein:

$R_1$ and $R_2$ are independently selected from the group consisting of methyl and ethyl, each methyl and ethyl optionally and independently substituted by a member selected from the group consisting of hydroxy and methoxy;

$R_3$ and $R_4$ are methyl;

$R_6$ is hydrogen or methyl;

$R_{13}$ is a member selected from the group consisting of hydrogen, formyl, methyl, ethyl or propyl, wherein each methyl, ethyl or propyl is optionally and independently substituted by fluoro or hydroxy;

$R_{14}$ is a member selected from the group consisting of bromo, iodo, formyl, methyl, and ethyl, wherein each methyl or ethyl is optionally and independently substituted by hydroxy; and $R_{15}$ is methyl.

11. A compound of the formula

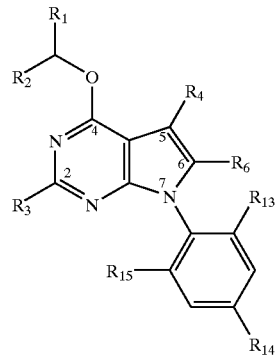

and prodrug and metabolite derivatives thereof affording pharmaceutically active species, and pharmaceutically acceptable acid addition salts thereof, wherein:

$R_1$ and $R_2$ are independently selected from the group consisting of hydrogen, methyl ethyl, n-propyl, n-butyl, s-butyl, n-pentyl, and n-hexyl, each methyl optionally and independently substituted by hydroxy, methoxy or amino:

$R_3$ is methyl;

$R_4$ is bromo or methyl;

$R_6$ is methyl, $R_{13}$ and $R_{15}$ are methyl; and $R_{14}$ is hydrogen or methyl.

12. A pharmaceutical composition for the treatment or prophylaxis of one or more diseases induced, mediated, facilitated, and/or characterized by elevated levels of corticotropin releasing factor in a mammal in need of such treatment or prophylaxis, said composition comprising:

(A) at least one compound of the formula

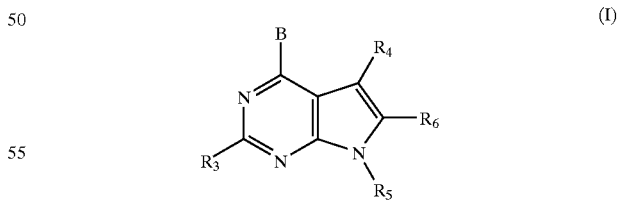

(I)

or a pharmaceutically acceptable acid addition salt thereof, wherein B is $NR_1R_2$, $CR_1R_2R_{11}$, $C(=CR_2R_{12})R_1$, $NH—CR_1R_2R_{11}$, $CR_2R_{11}NHR_1$, $CR_2R_{11}OR_1$, $CR_2R_{11}SR_1$, or $C(=O)R_2$; wherein $R_1$ is hydrogen, or monovalent $C_1$–$C_6$ aliphatic hydrocarbon which may be substituted by one or two substituents $R_7$ wherein $R_7$ is independently selected from the group consisting of hydroxy, fluoro, chloro, bromo, iodo, $C_1$-$C_6$ alkoxy, O—C(=O)—($C_1$-$C_6$ alkyl), O—C (=O)—NH($C_1$-$C_4$ alkyl), OC(=O)—N($C_1$-$C_4$ alkyl)($C_1$-$C_2$ alkyl), amino, NH($C_1$-$C_4$ alkyl), N($C_1$-$C_2$ alkyl)($C_1$-$C_4$ alkyl), S($C_1$-$C_6$ alkyl), N($C_1$-$C_4$ alkyl)—C(=O)—($C_1$-$C_4$ alkyl), NH—C(=O)—($C_1$-$C_4$ alkyl), C(=O)OH, C(=O)—O—($C_1$-$C_4$ alkyl), C(=O)—NH ($C_1$-$C_4$ alkyl), C(=O)—N—($C_1$-$C_4$ alkyl)($C_1$-$C_2$ alkyl), SH, CN, $NO_2$, SO($C_1$-$C_4$ alkyl), $SO_2$($C_1$-$C_4$ alkyl), $SO_2$NH($C_1$-$C_4$ alkyl), and $SO_2$N($C_1$-$C_4$ alkyl)($C_1$-$C_2$ alkyl); and wherein said monovalent $C_1$–$C_6$ aliphatic hydrocarbon [alkyl] may contain one or two double or triple bonds;

$R_2$ is monovalent $C_1$–$C_{12}$ aliphatic hydrocarbon; aryl; divalent ($C_1$-$C_{10}$ aliphatic hydrocarbon)aryl wherein said aryl is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzisothiazolyl, thiazolyl, isoxazolyl, benzisoxazolyl, benzimidazolyl, triazolyl, pyrazolyl, pyrrolyl, indolyl, pyrrolopyridyl, oxazolyl, or benzoxazolyl; 3- to 8-membered cycloalkyl; or ($C_1$-$C_6$ alkylene) cycloalkyl, wherein one or two methylene groups of said cycloalkyl may be independently replaced by one or two O, S or N—Z radicals wherein Z is hydrogen, $C_1$-$C_4$ alkyl, benzyl or $C_1$-$C_4$ alkanoyl, wherein $R_2$ may be substituted independently by from one to three of chloro, fluoro, or $C_1$-$C_4$ alkyl; or one of hydroxy, bromo, iodo, $C_1$-$C_6$ alkoxy, O—C(=O)—($C_1$-$C_6$ alkyl), O—C(=O)—N($C_1$-$C_4$ alkyl)($C_1$-$C_2$ alkyl), S(C, $C_6$ alkyl), $NH_2$, NH($C_1$-$C_2$ alkyl), N($C_1$-$C_2$ alkyl)($C_1$-$C_4$ alkyl), N($C_1$-$C_4$ alkyl)—C(=O)—($C_1$-$C_4$ alkyl), NH—C(=O)—($C_1$-$C_4$ alkyl), C(=O)OH, C(=O)—O—($C_1$-$C_4$ alkyl), C(=O)—NH—($C_1$-$C_4$ alkyl), C(=O)—N—($C_1$-$C_4$ alkyl)($C_1$-$C_2$ alkyl), SH, CN, $NO_2$, SO($C_1$-$C_4$ alkyl), $SO_2$($C_1$-$C_4$ alkyl), $SO_2$NH ($C_1$-$C_4$ alkyl), or $SO_2$N($C_1$-$C_4$ alkyl)($C_1$-$C_2$ alkyl), and wherein said monovalent $C_1$-$C_{12}$ aliphatic hydrocarbon or divalent $C_1$-$C_{10}$ aliphatic hydrocarbon may contain one to three double or triple bonds; or $NR_1R_2$ taken together or $CR_1R_2R_{11}$ taken together may form saturated 3- to 8-membered carbocyclic rings, wherein said rings having from 5 to 8 members may contain one or two double bonds or one or two O, S or N—Z radicals wherein Z is hydrogen, $C_1$-$C_4$ alkyl, benzyl or $C_1$-$C_4$ alkanoyl;

$R_3$ is hydrogen, monovalent $C_1$-$C_6$ aliphatic hydrocarbon, fluoro, chloro, bromo, iodo, hydroxy, amino, O(monovalent $C_1$-$C_6$ aliphatic hydrocarbon), NH(monovalent $C_1$-$C_6$ aliphatic hydrocarbon), N(monovalent $C_1$-$C_4$ aliphatic hydrocarbon)($C_1$-$C_2$ alkyl), SH, S(monovalent $C_1$-$C_4$ aliphatic hydrocarbon), SO(monovalent $C_1$-$C_4$ aliphatic hydrocarbon), or $SO_2$(monovalent $C_1$-$C_4$ aliphatic hydrocarbon), wherein said monovalent $C_1$-$C_4$ aliphatic hydrocarbon and said monovalent $C_1$-$C_6$ aliphatic hydrocarbon may contain one double or triple bond and may be substituted by from one to three substituents $R_8$ wherein R8 is independently selected from the group consisting of hydroxy, $C_1$-$C_3$ alkoxy, fluoro, chloro and $C_1$-$C_3$ alkylthio;

$R_4$ is hydrogen, $C_1$-$C_6$ alkyl, fluoro, chloro, bromo, iodo, $C_1$-$C_6$ alkoxy, amino, NH($C_1$-$C_6$ alkyl), N($C_1$-$C_6$ alkyl)($C_1$-$C_2$ alkyl), $SO_n$($C_1$-$C_6$ alkyl), wherein n is 0, 1 or 2, cyano, hydroxy, carboxy, or amido, wherein said $C_1$-$C_6$ alkyls may be substituted by one hydroxy, trifluoromethyl, amino, carboxy, amido, NH—C(=O)—($C_1$-$C_4$ alkyl), NH($C_1$-$C_4$ alkyl), N($C_1$-$C_4$ alkyl)($C_1$-$C_2$ alkyl), C(=O)—O—($C_1$-$C_4$ alkyl), $C_1$-$C_3$ alkoxy, $C_1$-$C_3$ alkylthio, fluoro, bromo, chloro, iodo, cyano or nitro;

$R_5$ is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzisothiazolyl, thiazolyl, isoxazolyl, benzisoxazolyl, benzimidazolyl, triazolyl, pyrazolyl, pyrrolyl, indolyl, azaindolyl, benzoxazolyl, oxazolyl, pyrrolidinyl, thiazolidinyl, morpholinyl, piperidinyl, piperazinyl, tetrazolyl, or 3- to 8-membered cycloalkyl or 9 to 12-membered bicycloalkyl, optionally containing one or two O, S or N—Z radicals wherein Z is hydrogen, $C_1$-$C_4$ alkyl, $C_1$-$C_4$ alkanoyl, phenyl or phenylmethyl; wherein each one of the above groups may be substituted independently by from one to three of fluoro, chloro, bromo, formyl, monovalent $C_1$-$C_6$ aliphatic hydrocarbon, $C_1$-$C_6$ alkoxy or trifluoromethyl, or one of hydroxy, iodo, cyano, nitro, amino, NH(monovalent $C_1$-$C_4$ aliphatic_hydrocarbon), N(monovalent $C_1$-$C_4$ aliphatic hydrocarbon)($C_1$-$C_2$ alkyl), COO(monovalent $C_1$-$C_4$ aliphatic hydrocarbon), CO(monovalent $C_1$-$C_4$ aliphatic hydrocarbon), $SO_2$NH-(monovalent $C_1$-$C_4$ aliphatic hydrocarbon), $SO_2$N(monovalent $C_1$-$C_4$ aliphatic hydrocarbon)($C_1$-$C_2$ alkyl), $SO_2NH_2$, $NHSO_2$ (monovalent $C_1$-$C_4$ aliphatic hydrocarbon), S(monovalent $C_1$-$C_4$ aliphatic hydrocarbon), or $SO_2$ (monovalent $C_1$-$C_4$ aliphatic hydrocarbon), wherein said monovalent $C_1$-$C_4$ aliphatic hydrocarbon and said monovalent $C_1$-$C_6$ aliphatic hydrocarbon may be substituted by one or two of fluoro, chloro, hydroxy, $C_1$–$C_4$ alkoxy, amino, methylamino, dimethylamino or acetyl; and wherein said monovalent $C_1$-$C_4$ aliphatic hydrocarbon and said monovalent $C_1$-Co aliphatic hydrocarbon may contain one double or triple bond;

$R_6$ is hydrogen, $C_1$-$C_6$ alkyl, fluoro, chloro, bromo, iodo, $C_1$-$C_6$ alkoxy, formyl, amino, NH($C_1$-$C_6$ alkyl), N($C_1$-$C_6$ alkyl)($C_1$-$C_2$ alkyl), $SO_n$($C_1$-$C_6$ alkyl) wherein n is 0, 1 or 2, cyano, carboxy, or amido, wherein said $C_1$-$C_6$ alkyls may be substituted by one hydroxy, trifluoromethyl, amino, carboxy, amido, NH—C(=O)—($C_1$-$C_4$ alkyl), NH($C_1$-$C_4$ alkyl), N($C_1$-$C_4$ alkyl)($C_1$-$C_2$ alkyl), C(=O)—O—($C_1$-$C_4$ alkyl), $C_1$-$C_3$ alkoxy, $C_1$-$C_3$ alkylthio, fluoro, bromo, chloro, iodo, cyano or nitro;

$R_{11}$ is hydrogen, hydroxy, fluoro, chloro, C(=O)—O—($C_1$-$C_2$ alkyl), cyano, or C(=O)($C_1$-$C_2$ alkyl); and $R_{12}$ is hydrogen or $C_1$-$C_4$ alkyl, that is effective in treating such disorder;

WITH THE PROVISO THAT:
  (1) when $R_5$ is p-bromophenyl, and $R_3$, $R_4$ and $R_6$ are methyl, then B is not methylamino or hydroxyethylamino;
  (2) when $R_5$ is unsubstituted phenyl or unsubstituted cycloalkyl, then R3 and R4 are hydrogen, and $R_6$ is hydrogen or methyl, then B is not NH substituted by furanylmethyl, benzyl, or thienylmetyl;
  (3) when B represents $CR_1R_2R_{11}$ and both of $R_1$ and $R_{11}$ represent hydrogen, then $R_2$ does not represent straight chain $C_1$–$C_{12}$ alkyl;
  (4) when $R_5$ is p-bromophenyl, $R_4$ and $R_6$ are methyl and $R_3$ is hydrogen, then B does not represent thioethyl or methylamino; and
  (5) when $R_5$ is substituted cyclobutane, then $R_4$ is ($C_1$–$C_6$) alkyl;
that is effective in treating or preventing said disease.

13. A pharmaceutical composition according to claim 12 wherein said disease comprises one or more members selected from the group consisting of stress-related illnesses; gastronintestinal diseases and bowel disorders; Inflammatory disorders; mental, neural and central nervous system diseases and disorders; fertility disfunctions; cancer; and human immunodeficiency virus,infections.

14. A pharmaceutical composition according to claim 13 wherein said stress-related illnesses comprise stress-induced depression, fatigue syndrome, or stress-induced psychotic episodes; said gastronintestinal diseases and bowel disorders comprise Irritable bowel syndrome, Crohn's disease, spastic colon or irritable colon; said inflammatory disorders comprise arthritis, asthma, pain or immune dysfunction; and said mental, neural and central nervous system diseases and disorders comprise anxiety, depression, fatigue syndrome, headache, pain, neurodegenerative diseases, Alzheimer's disease, eating disorders, anorexia nervosa, drug addiction, drug and alcohol withdrawal symptoms, or stress-induced psychotic episodes.

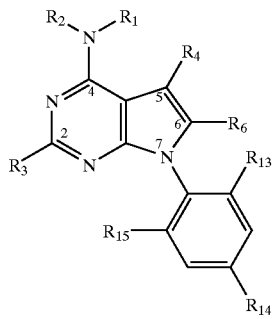

15. A method of treating or preventing one or more diseases induced, mediated, facilitated, and/or characterized by elevated levels of corticotropin releasing factor in a mammal in need of such treatment or prevention, comprising administering to said mammal an therapeuticaly or prophylactically effective amount of a compound of the formula

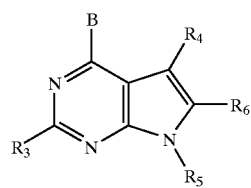

(I)

or a pharmaceutically acceptable acid addition salt thereof, wherein B is $NR_1R_2$, $CR_1R_2R_{11}$, $C(=CR_2R_{12})R_1$, $NH-CR_1R_2R_{11}$, $CR_2R_{11}NHR_1$, $CR_2R_{11}OR_1$, $CR_2R_{11}SR_1$, or $C(=O)R_2$; wherein:

$R_1$ is hydrogen, or monovalent $C_1$–$C_6$ aliphatic hydrocarbon which may be substituted by one or two substituents $R_7$ wherein R7 is independently selected from the group consisting of hydroxy, fluoro, chloro, bromo, iodo, $C_1$-$C_6$ alkoxy, O—C(=O)—($C_1$-$C_6$ alkyl), O—C(=O)—NH($C_1$-$C_4$ alkyl), O—C(=O)—N($C_1$-$C_4$ alkyl)($C_1$-$C_4$ alkyl), amino, NH($C_1$-$C_4$ alkyl), N($C_1$-$C_2$ alkyl)($C_1$-$C_4$ alkyl), S($C_1$-$C_6$ alkyl), N($C_1$-$C_4$ alkyl)—C(=O)—($C_1$-$C_4$ alkyl), NH—C(=O)—($C_1$-$C_4$ alkyl), C(=O)OH, C(=O)—O—($C_1$-$C_4$ alkyl), C(=O)—NH ($C_1$-$C_4$ alkyl), C(=O)—N—($C_1$-$C_4$ alkyl)($C_1$-$C_2$ alkyl), SH, CN, $NO_2$, SO($C_1$-$C_4$ alkyl), $SO_2$($C_1$-$C_4$ alkyl), $SO_2NH$($C_1$-$C_4$ alkyl), and $SO_2N$($C_1$-$C_4$ alkyl)($C_1$-$C_2$ alkyl); and wherein said monovalent $C_1$–$C_6$ aliphatic hydrocarbon may contain one or two double or triple bonds;

$R_2$ is monovalent $C_1$–$C_{12}$ aliphatic hydrocarbon; aryl; divalent($C_1$–$C_{10}$ aliphatic hydrocarbon)aryl wherein said aryl is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzisothiazolyl, thiazolyl, isoxazolyl, benzisoxazolyl, benzimidazolyl, triazolyl, pyrazolyl, pyrrolyl, indolyl, pyrrolopyridyl, oxazolyl, or benzoxazolyl; 3- to 8-membered cycloalkyl; or ($C_1$-$C_6$ alkylene) cycloalkyl, wherein one or two methylene groups of said cycloalkyl may be independently replaced by one or two O, S or N—Z radicals wherein Z is hydrogen, $C_1$-$C_4$ alkyl, benzyl or $C_1$-$C_4$ alkanoyl, wherein $R_2$ may be substituted independently by from one to three of chloro, fluoro, or $C_1$-$C_4$ alkyl; or one of hydroxy, bromo, iodo, $C_1$-$C_6$ alkoxy, O—C(=O)—($C_1$-$C_6$ alkyl), O—C(=O)—N($C_1$-$C_4$ alkyl)($C_1$-$C_2$ alkyl), S($C_1$-$C_6$ alkyl), $NH_2$, NH($C_1$-$C_2$ alkyl), N($C_1$-$C_2$alkyl)($C_1$-$C_4$ alkyl), N($C_1$-$C_4$ alkyl)—C(=O)—($C_1$-$C_4$ alkyl), NH—C(=O)—($C_1$-$C_4$ alkyl), C(=O)OH, C(O)O—($C_1$-$C_4$ alkyl), C(=O)—NH—($C_1$-$C_4$ alkyl), C(=O)—N—($C_1$-$C_4$ alkyl)($C_1$-$C_2$ alkyl), SH, CN, $NO_2$, SO($C_1$-$C_4$ alkyl), $SO_2$($C_1$-$C_4$ alkyl), $SO_2NH$($C_1$-$C_4$ alkyl), or $SO_2N$($C_1$-$C_4$ alkyl)($C_1$-$C_2$ alkyl), and wherein said monovalent $C_1$–$C_{12}$ aliphatic hydrocarbon or divalent $C_1$–$C_{10}$ aliphatic hydrocarbon may contain one to three double or triple bonds; or $NR_1R_2$ taken together or $CR_1R_2R_{11}$ taken together may form saturated 3 to 8-membered carbocyclic rings, wherein said rings having from 5 to 8 members may contain one or two double bonds or one or two O, S or N—Z radicals wherein Z is hydrogen, $C_1$-$C_4$ alkyl, benzyl or $C_1$-$C_4$ alkanoyl;

$R_3$ is hydrogen, monovalent $C_1$-$C_6$ aliphatic hydrocarbon, fluoro, chloro, bromo, iodo, hydroxy,amino, O(monovalent $C_1$-$C_6$ aliphatic hydrocarbon), NH(monovalent $C_1$-$C_6$ aliphatic hydrocarbon), N(monovalent $C_1$-$C_4$ aliphatic hydrocarbon)($C_1$-$C_2$ alkyl), SH, S(monovalent $C_1$-$C_4$ aliphatic hydrocarbon), SO(monovalent $C_1$-$C_4$ aliphatic hydrocarbon), or $SO_2$(monovalent $C_1$-$C_4$ aliphatic hydrocarbon), wherein said monovalent $C_1$-$C_4$ aliphatic hydrocarbon and said monovalent $C_1$-$C_6$ aliphatic hydrocarbon may contain one double or triple bond and may be substituted by from one to three substituents $R_8$ wherein R8 is independently selected from the group consisting of hydroxy, $C_1$-$C_3$ alkoxy, fluoro, chloro and $C_1$-$C_3$ alkylthio;

$R_4$ is hydrogen, $C_1$-$C_6$ alkyl, fluoro, chloro, bromo, iodo, $C_1$-$C_6$ alkoxy, amino, NH($C_1$-$C_6$ alkyl), N($C_1$-$C_6$ alkyl) ($C_1$-$C_2$ alkyl), $SO_n$($C_1$-$C_6$ alkyl), wherein n is 0, 1 or 2, cyano, hydroxy, carboxy, or amido, wherein said $C_1$-$C_6$ alkyls may be substituted by one hydroxy, trifluoromethyl, amino, carboxy, amido, NH—C (=O)—($C_1$-$C_4$ alkyl), NH($C_1$-$C_4$ alkyl), N($C_1$-$C_4$ alkyl)($C_1$-$C_2$alkyl), C(=O)—O—($C_1$-$C_4$alkyl), $C_1$-$C_3$ alkoxy, $C_1$-$C_3$ alkylthio, fluoro, bromo, chloro, iodo, cyano or nitro;

$R_5$ is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzisothiazolyl, thiazolyl, isoxazolyl, benzisoxazolyl, benzimidazolyl, triazolyl, pyrazolyl, pyrrolyl, indolyl, azaindolyl, benzoxazolyl, oxazolyl, pyrrolidinyl, thiazolidinyl, morpholinyl, piperidinyl, piperazinyl, tetrazolyl, or 3- to 8-membered cycloalkyl or 9- to 12-membered bicycloalkyl, optionally containing one or two O, S or N—Z radicals wherein Z is hydrogen, $C_1$-$C_4$ alkyl, $C_1$-$C_4$ alkanoyl, phenyl or phenylmethyl; wherein each one of the above groups may be substituted independently by from one to three of fluoro, chloro, bromo, formyl, monovalent $C_1$-$C_6$ aliphatic hydrocarbon, $C_1$-$C_6$ alkoxy or trifluoromethyl, or one of hydroxy, iodo, cyano, nitro, amino, NH(monovalent $C_1$-$C_4$ aliphatic hydrocarbon), N(monovalent $C_1$-$C_4$ aliphatic hydrocarbon)($C_1$-$C_2$ alkyl), COO (monovalent $C_1$-$C_4$ aliphatic hydrocarbon), CO(monovalent $C_1$-$C_4$ aliphatic hydrocarbon), $SO_2$NH-(monovalent $C_1$-$C_4$ aliphatic hydrocarbon), $SO_2$N(monovalent $C_1$-$C_4$ aliphatic hydrocarbon)($C_1$-$C_2$ alkyl), $SO_2NH_2$, $NHSO_2$(monovalent $C_1$-$C_4$ aliphatic hydrocarbon), S(monovalent $C_1$-$C_6$ aliphatic hydrocarbon), or $SO_2$(monovalent $C_1$-$C_6$ aliphatic hydrocarbon), wherein said monovalent $C_1$-$C_4$ aliphatic hydrocarbon and said monovalent $C_1$-$C_6$ aliphatic hydrocarbon may be substituted by one or two of fluoro, chloro, hydroxy, $C_1$-$C_4$ alkoxy, amino, methylamino, dimethylamino or acetyl; and wherein said monovalent $C_1$-$C_4$ aliphatic hydrocarbon and said monovalent $C_1$-$C_6$ aliphatic hydrocarbon may contain one double or triple bond;

$R_6$ is hydrogen, $C_1$-$C_6$ alkyl, fluoro, chloro, bromo, iodo, $C_1$-$C_6$ alkoxy, formyl, amino, NH($C_1$-$C_6$ alkyl), N($C_1$-$C_6$ alkyl)($C_1$-$C_2$ alkyl), $SO_n$($C_1$-$C_6$ alkyl) wherein n is 0, 1 or 2, cyano, carboxy, or amido, wherein said $C_1$-$C_6$ alkyls may be substituted by one hydroxy, trifluoromethyl, amino, carboxy, amido, NH—C(=O)—($C_1$-$C_4$ alkyl), NH($C_1$-$C_4$alkyl), N($C_1$-$C_4$alkyl)($C_1$-$C_2$ alkyl), C(=O)—O—($C_1$-$C_4$ alkyl), $C_1$-$C_3$ alkoxy, $C_1$-$C_3$ alkylthio, fluoro, bromo, chloro, iodo, cyano or nitro;

$R_{11}$ is hydrogen, hydroxy, fluoro, chloro, C(=O)—O—($C_1$-$C_2$ alkyl), cyano, or C(=O)($C_1$-$C_2$ alkyl); and $R_{12}$ is hydrogen or $C_1$-$C_4$ alkyl, that is effective in treating such disorder;

WITH THE PROVISO THAT:
(1) when $R_5$ is p-bromophenyl, and $R_3$, $R_4$ and $R_6$ are methyl, then B is not methylamino or hydroxyethylamino;
(2) when $R_5$ is unsubstituted phenyl or unsubstituted cycloalkyl, then $R_3$ and $R_4$ are hydrogen, and $R_6$ is hydrogen or methyl, then B is not NH substituted by furanylmethyl, benzyl, or thienylmetyl;
(3) when B represents $CR_1R_2R_{11}$ and both of $R_1$ and $R_{11}$ represent hydrogen, then $R_2$ does not represent straight chain $C_1$-$C_{12}$ alkyl;
(4) when $R_5$ is p-bromophenyl, $R_4$ and $R_6$ are methyl and $R_3$ is hydrogen, then B does not represent thioethyl or methylamino: and
(5) when $R_5$ is substituted cyclobutane, then $R_4$ is ($C_1$-$C_6$) alkyl;

that is effective In treating or preventing said disease.

16. A method of treating or preventing depression which is induced, mediated, facilitated, and/or characterized by elevated levels of corticotropin releasing factor in a mammal in need of such treatment or prevention, comprising administering to said mammal a therapeuticaly or prophylactically effective amount of a compound of the formula

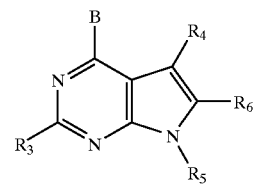

or a pharmaceutically acceptable acid addition salt thereof, wherein B is $NR_1R_2$, $CR_1R_2R_{11}$, C(=$CR_2R_{12}$)$R_1$, NH—$CR_1R_2R_{11}$, $CR_2R_{11}NHR_1$, $CR_2R_{11}OR_1$, $CR_2R$, $SR_1$, or C(=O)$R_2$; wherein $R_1$ is hydrogen, or monovalent $C_1$-$C_6$ aliphatic hydrocarbon which may be substituted by one or two substituents $R_7$ wherein R7 is independently selected from the group consisting of hydroxy, fluoro, chloro, bromo, iodo, $C_1$-$C_6$ alkoxy, O—C(=O)$C_1$-$C_6$ alkyl), O—C(=O)—NH($C_1$-$C_4$ alkyl), O—C(=O)—N($C_1$-$C_4$ alkyl)($C_1$-$C_2$ alkyl), amino, NH($C_1$-$C_4$ alkyl), N($C_1$-$C_2$ alkyl)($C_1$-$C_4$ alkyl), S($C_1$-$C_6$alkyl), N($C_1$-$C_4$ alkyl)—C(=O)—($C_1$-$C_4$ alkyl), NH—C(=O)—($C_1$-$C_4$ alkyl), C(=O)OH, C(=O)—O—($C_1$-$C_4$ alkyl), C(=O)—NH($C_1$-$C_4$ alkyl), C(=O)—N—($C_1$-$C_4$ alkyl)($C_1$-$C_2$alkyl), SH, CN, $NO_2$, SO($C_1$-$C_4$ alkyl), $SO_2$($C_1$-$C_4$ alkyl), $SO_2$NH($C_1$-$C_4$alkyl), and $SO_2$N($C_1$-$C_4$alkyl)($C_1$-$C_2$alkyl); and wherein said monovalent $C_1$-$C_6$ aliphatic hydrocarbon may contain one or two double or triple bonds;

$R_2$ is monovalent $C_1$-$C_{12}$ aliphatic hydrocarbon; aryl; divalent ($C_1$-$C_{10}$ aliphatic hydrocarbon)aryl wherein said aryl is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzisothiazolyl, thiazolyl, isoxazolyl, benzisoxazolyl, benzimidazolyl, triazolyl, pyrazolyl, pyrrolyl, indolyl, pyrrolopyridyl, oxazolyl, or benzoxazolyl; 3- to 8-membered cycloalkyl; or ($C_1$-$C_6$ alkylene) cycloalkyl, wherein one or two methylene groups of said cycloalkyl may be independently replaced by one or two O, S or N—Z radicals wherein Z is hydrogen, $C_1$-$C_4$ alkyl, benzyl or $C_1$-$C_4$ alkanoyl, wherein $R_2$ may be substituted independently by from one to three of chloro, fluoro, or $C_1$-$C_4$ alkyl; or one of hydroxy, bromo, iodo, $C_1$-$C_6$ alkoxy, O—C(=O)—($C_1$-$C_6$ alkyl), O—C(=O)—N($C_1$-$C_4$ alkyl)($C_1$-$C_2$ alkyl), S($C_1$-$C_6$ alkyl), $NH_2$, NH($C_1$-$C_2$ alkyl), N($C_1$-$C_2$alkyl)($C_1$-$C_4$ alkyl), N($C_1$-$C_4$ alkyl)—C(=O)—($C_1$-$C_4$ alkyl), NH—C(=O)—($C_1$-$C_4$ alkyl), C(=O)OH, C(=O)—O—($C_1$-$C_4$ alkyl), C(=O)—NH—($C_1$-$C_4$ alkyl), C(=O)—N—($C_1$-$C_4$ alkyl)($C_1$-$C_2$ alkyl), SH, CN, $NO_2$, SO($C_1$-$C_4$ alkyl), $SO_2$($C_1$-$C_4$ alkyl), $SO_2$NH ($C_1$-$C_4$ alkyl), or $SO_2$N($C_1$-$C_4$ alkyl)($C_1$-$C_2$ alkyl), and wherein said monovalent $C_1$-$C_{12}$ aliphatic hydrocarbon or divalent ($C_1$-$C_{10}$ aliphatic hydrocarbon) may contain one to three double or triple bonds; or $NR_1R_2$ or $CR_1R_2R_1$, taken together may form saturated 3- to 8-membered carbocyclic rings, wherein said rings having from 5 to 8 members may contain one or two double bonds or one or two O, S or N—Z radicals wherein Z is hydrogen, $C_1$-$C_4$ alkyl, benzyl or $C_1$-$C_4$ alkanoyl;

$R_3$ is hydrogen, monovalent $C_1$-$C_6$ aliphatic hydrocarbon, fluoro, chloro, bromo, iodo, hydroxy, amino, O(monovalent $C_1$-$C_6$ aliphatic hydrocarbon), NH(monovalent $C_1$-$C_6$ aliphatic hydrocarbon), N(monovalent $C_1$-$C_4$ aliphatic hydrocarbon)($C_1$-$C_2$ alkyl), SH, S(monovalent $C_1$-$C_4$ aliphatic hydrocarbon), SO(monovalent $C_1$-$C_4$ aliphatic hydrocarbon), or $SO_2$(monovalent $C_1$-$C_4$ aliphatic hydrocarbon), wherein said monovalent $C_1$-$C_4$ aliphatic hydrocarbon and said monovalent $C_1$-$C_6$ aliphatic hydrocarbon may contain one double or triple bond and may be substituted by from one to three substituents $R_8$ wherein R8 is independently selected from the group consisting of hydroxy, $C_1$-$C_3$ alkoxy, fluoro, chloro and $C_1$-$C_3$ alkylthio;

$R_4$ is hydrogen, $C_1$-$C_6$ alkyl, fluoro, chloro, bromo, iodo, $C_1$-$C_6$ alkoxy, amino, NH($C_1$-$C_6$ alkyl), N($C_1$-$C_6$ alkyl)($C_1$-$C_2$ alkyl), $SO_n$($C_1$-$C_6$ alkyl), wherein n is 0, 1 or 2, cyano, hydroxy, carboxy, or amido, wherein said $C_1$-$C_6$ alkyls may be substituted by one hydroxy, trifluoromethyl, amino, carboxy, amido, NH—C(=O)—($C_1$-$C_4$ alkyl), NH($C_1$-$C_4$ alkyl), N($C_1$-$C_4$ alkyl)($C_1$-$C_2$ alkyl), C(=O)—O—($C_1$-$C_4$ alkyl), $C_1$-$C_3$ alkoxy, $C_1$-$C_3$ alkylthio, fluoro, bromo, chloro, iodo, cyano or nitro;

$R_5$ is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzisothiazolyl, thiazolyl, isoxazolyl, benzisoxazolyl, benzimidazolyl, triazolyl, pyrazolyl, pyrrolyl, indolyl, azaindolyl, benzoxazolyl, oxazolyl, pyrrolidinyl, thiazolidinyl, morpholinyl, piperidinyl, piperazinyl, tetrazolyl, or 3- to 8-membered cycloalkyl or 9- to 12-membered bicycloalkyl, optionally containing one or two of O, S or N—Z radicals wherein Z is hydrogen, $C_1$-$C_4$ alkyl, $C_1$-$C_4$ alkanoyl, phenyl or phenylmethyl; wherein each one of the above groups may be substituted independently by from one to three of fluoro, chloro, bromo, formyl, monovalent $C_1$-$C_6$ aliphatic hydrocarbon, $C_1$-$C_6$ alkoxy or trifluoromethyl, or one of bromo, iodo, cyano, nitro, amino, NH(monovalent $C_1$-$C_4$ aliphatic hydrocarbon), N(monovalent $C_1$-$C_4$ aliphatic hydrocarbon)($C_1$-$C_2$ alkyl), COO(monovalent $C_1$-$C_4$ aliphatic hydrocarbon), CO(monovalent $C_1$-$C_4$ aliphatic hydrocarbon), $SO_2$NH—(monovalent $C_1$-$C_4$ aliphatic hydrocarbon), $SO_2$N(monovalent $C_1$-$C_4$ aliphatic hydrocarbon)($C_1$-$C_2$ alkyl), $SO_2NH_2$, $NHSO_2$(monovalent $C_1$-$C_4$ aliphatic hydrocarbon), S(monovalent $C_1$-$C_6$ aliphatic hydrocarbon), or $SO_2$(monovalent $C_1$-$C_6$ aliphatic hydrocarbon), wherein said monovalent $C_1$-$C_4$ aliphatic hydrocarbon and said monovalent $C_1$-$C_6$ aliphatic hydrocarbon may be substituted by one or two of fluoro, chloro, hydroxy, amino, methylamino, dimethylamino or acetyl wherein said monovalent $C_1$-$C_4$ aliphatic hydrocarbon and said monovalent $C_1$-$C_6$ aliphatic hydrocarbon may contain one double or triple bond;

$R_6$ is hydrogen, $C_1$-$C_6$ alkyl, fluoro, chloro, bromo, iodo, $C_1$-$C_6$ alkoxy, formyl, amino, NH($C_1$-$C_6$ alkyl), N($C_1$-$C_6$ alkyl)($C_1$-$C_2$ alkyl), $SO_n$($C_1$-$C_6$ alkyl) wherein n is 0, 1 or 2, cyano, carboxy, or amido, wherein said $C_1$-$C_6$ alkyls may be substituted by one hydroxy, trifluoromethyl, amino, carboxy, amido, NH—C(=O)—($C_1$-$C_4$ alkyl), NH($C_1$-$C_4$ alkyl), N($C_1$-$C_4$ alkyl)($C_1$-$C_2$ alkyl), C(=O)—O—($C_1$-$C_4$ alkyl), $C_1$-$C_3$ alkoxy, $C_1$-$C_3$ alkylthio, fluoro, bromo, chloro, iodo, cyano or nitro;

$R_{11}$ is hydrogen, hydroxy, fluoro, chloro, C(=O)—O—($C_1$-$C_2$ alkyl), cyano, or C(=O)($C_1$-$C_2$ alkyl); and $R_{12}$ is hydrogen or $C_1$-$C_4$ alkyl, WITH THE PROVISO THAT:
(1) when $R_6$ is p-bromophenyl, and $R_3$, $R_4$ and $R_6$ are methyl, then B is not methylamino or hydroxyethylamino;
(2) when $R_5$ is unsubstituted phenyl or unsubstituted cycloalkyl, then $R_3$ and $R_4$ are hydrogen, and $R_6$ is hydrogen or methyl, then B is not NH substituted by furanylmethyl, benzyl, or thienylmetyl;
(3) when B represents $CR_1R_2R_{11}$ and both of $R_1$ and $R_{11}$ represent hydrogen, then $R_2$ does not represent straight chain $C_1$–$C_{12}$ alkyl;
(4) when $R_5$ is p-bromophenyl, $R_4$ and $R_6$ are methyl and $R_3$ is hydrogen, then B does not represent thioethyl or methylamino; and
(5) when $R_5$ is substituted cyclobutane, then $R_4$ is ($C_1$–$C_6$) alkyl;

that is effective in treating or preventing said disease.

17. A method of treating or preventing a disease according to claim 15 wherein said disease comprises one or more members selected from the group consisting of stress-related illnesses; gastronintestinal diseases and bowel disorders; inflammatory disorders; mental, neural and central nervous system diseases and disorders; fertility disfunctions; cancer; and human immunodeficiency virus infections.

18. A method of treating or preventing a disease according to claim 17 wherein said stress-related illnesses comprise stress-induced depression, fatigue syndrome, or stress-induced psychotic episodes; said gastronintestinal diseases and bowel disorders comprise irritable bowel syndrome, Crohn's disease, spastic colon or irritable colon; said inflammatory disorders comprise arthritis, asthma, pain or immune dysfunction; and said mental, neural and central nervous system diseases and disorders comprise anxiety, depression, fatigue syndrome, headache, pain, neurodegenerative diseases, Alzheimer's disease, eating disorders, anorexia nervosa, drug addiction, drug and alcohol withdrawal symptoms, or stress-induced psychotic episodes.

* * * * *